United States Patent [19]
Zhu et al.

[11] Patent Number: 5,407,427
[45] Date of Patent: Apr. 18, 1995

[54] TROCAR FACILITATOR FOR ENDOSCOPIC SURGERY

[75] Inventors: Yong H. Zhu, Loma Linda; Wolff M. Kirsch, Redlands, both of Calif.

[73] Assignee: Loma Linda University Medical Center, Loma Linda, Calif.

[21] Appl. No.: 29,116

[22] Filed: Mar. 10, 1993

Related U.S. Application Data

[63] Continuation-in-part of Ser. No. 899,605, Jun. 16, 1992, abandoned.

[51] Int. Cl.⁶ ............................................. A61B 17/34
[52] U.S. Cl. .................................... 604/26; 606/185; 604/272
[58] Field of Search ................. 606/185, 222; 604/26, 604/164, 272, 264

[56] References Cited

U.S. PATENT DOCUMENTS

| | | | |
|---|---|---|---|
| 67,545 | 8/1867 | Hodgins | 606/222 |
| 3,653,388 | 4/1972 | Tenchkhoff . | |
| 3,856,021 | 12/1974 | McIntosh . | |
| 3,893,454 | 7/1975 | Hagelin . | |
| 4,204,541 | 5/1980 | Kapitanov | 606/145 |
| 4,578,061 | 3/1986 | Lemelson | 604/164 |
| 4,585,437 | 4/1986 | Simms . | |
| 4,869,717 | 9/1989 | Adair | 604/26 X |
| 5,002,557 | 3/1991 | Hasson | 604/26 X |
| 5,009,643 | 4/1991 | Reich et al. . | |
| 5,139,485 | 8/1992 | Smith et al. | 604/26 X |
| 5,183,465 | 2/1993 | Xanthakos . | |
| 5,248,298 | 9/1993 | Bedi et al. . | |
| 5,261,888 | 11/1993 | Semm . | |
| 5,279,567 | 1/1994 | Ciaglia et al. . | |

FOREIGN PATENT DOCUMENTS

| | | | |
|---|---|---|---|
| 0487175 | 5/1992 | European Pat. Off. . | |
| 748666 | 7/1993 | France . | |
| 3321621 | 10/1984 | Germany . | |
| 3713831 | 12/1988 | Germany . | |
| 9102553 | 5/1991 | Germany . | |
| 9106553 | 8/1991 | Germany . | |
| 2154608 | 9/1985 | United Kingdom . | |
| 1331495 | 8/1987 | U.S.S.R. | 606/222 |
| 1528465 | 12/1989 | U.S.S.R. | 606/185 |
| 9221294 | 12/1992 | WIPO . | |

OTHER PUBLICATIONS

Commercial Advertisement—"Disposal Surgiport ® and Surgineedle ® Instruments Save Money!", Auto Suture Company, 1988.
H. M. Hasson, M.D., *Technique of Open Laparoscopy*, May 1979.
"Laparoscopic Principles and Techniques," *Principles of Endoscopic Surgery*, pp. 86-91, [unknown date].
Carl A. Zucker, M.D. and Robert W. Bailey, M.D., *Atlas of Endo Cholecystectomy with Auto Suture ® Instruments*, [unknown date].

*Primary Examiner*—Michael H. Thaler
*Attorney, Agent, or Firm*—Knobbe, Martens, Olson & Bear

[57] ABSTRACT

A trocar system for assisting in the generation of endosurgical ports is disclosed in which a trocar facilitator is used to place the peritoneum in counter-traction to facilitate the penetration of the trocar. Peritoneal counter-traction results in increased surface tension which reduces the force and downward momentum necessary to achieve trocar penetration, thereby eliminating the risk of excess penetration and injury to internal organs. The facilitator is of a corkscrew-like design, with an attached support ring and a removable guide piece having a hollow, cylindrical passageway which aids in the insertion and support of the trocar, cannula, and other endoscopic surgical instruments. In another embodiment, the facilitator is configured to aid in the introduction of carbon dioxide gas into the abdominal cavity of the patient. An improved curved tip of the blade of the trocar facilitator is also disclosed.

10 Claims, 24 Drawing Sheets

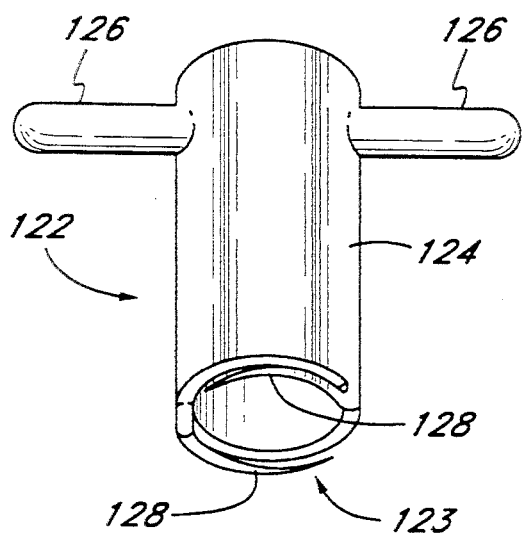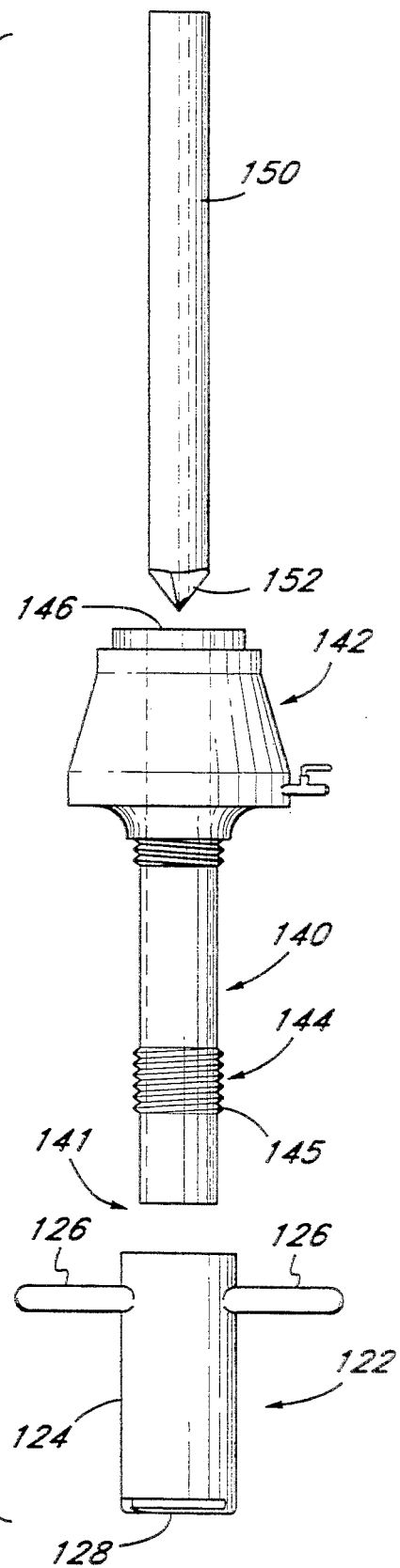

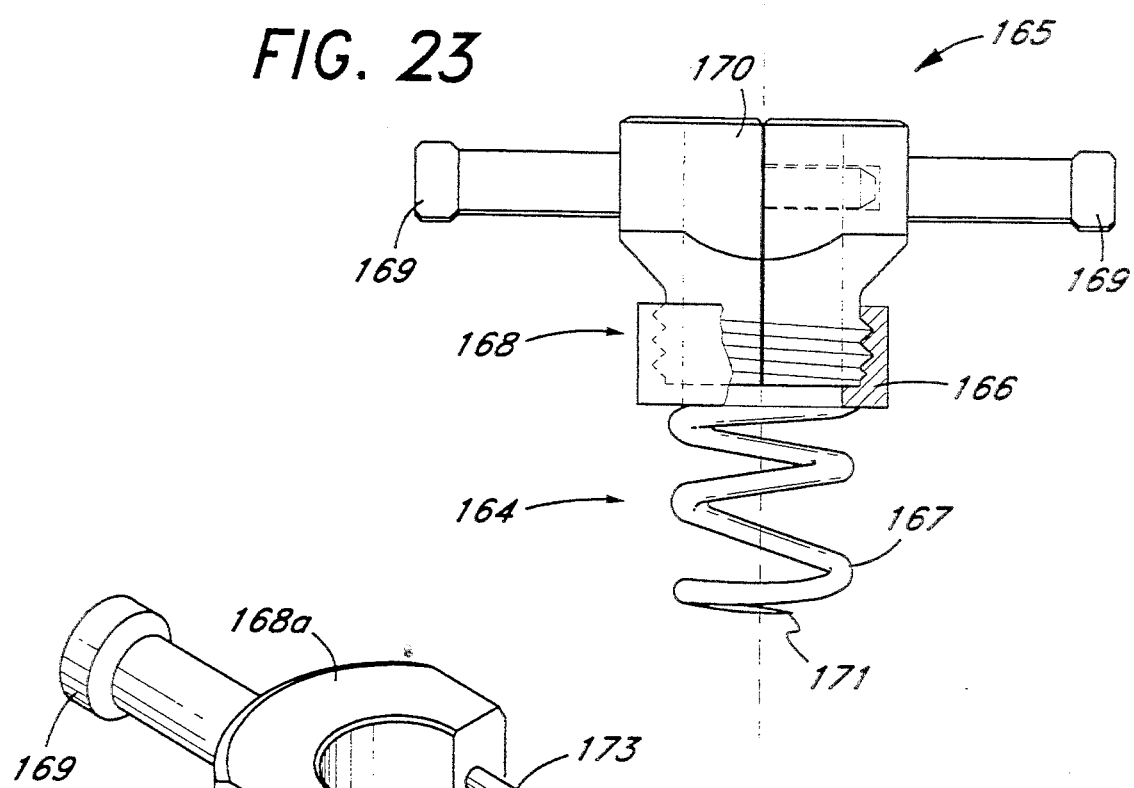
FIG. 23
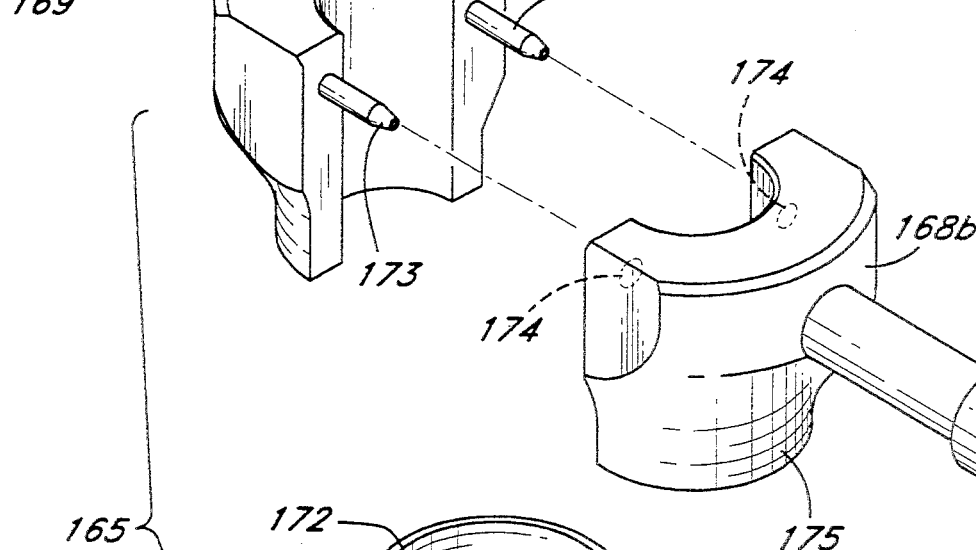
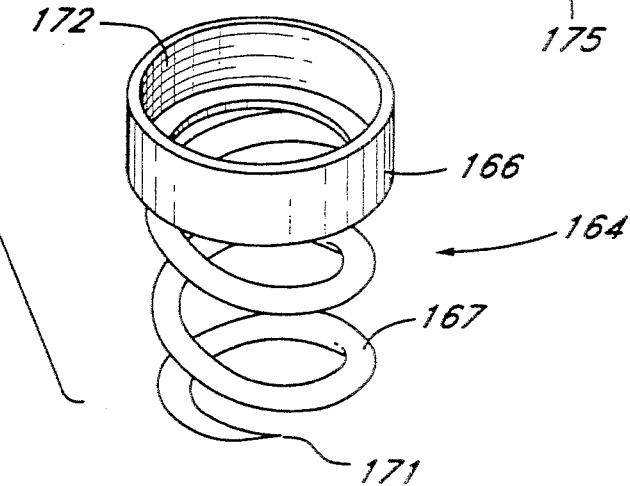
FIG. 24

TROCAR FACILITATOR FOR ENDOSCOPIC SURGERY

RELATED APPLICATIONS

This application is a continuation-in-part of U.S. patent application Ser. No. 07/899,605, filed Jun. 16, 1992, now abandoned.

FIELD OF THE INVENTION

The present invention relates to a trocar facilitator and, more specifically, to a facilitator having a countertraction mechanism to aid in the penetration of the trocar into a patient's body while eliminating the previous risks associated with trocar use.

BACKGROUND OF THE INVENTION

Endoscopic surgery is a procedure by which operations on internal portions of a patient's body are performed on a minimally intrusive basis. Such surgery is accomplished by creating small incisions or ports in the patient's body through which various small, remotely controllable instruments may be manipulated. The procedure is accomplished visually with the aid of an endoscope, hence the name endoscopic surgery. Substantial advantages are realized from this form of surgery, including reduced trauma to the patient, less risk of death or complications, and rapid recovery.

The endoscope is a thin, tubular instrument utilizing fiber optics which allows a surgeon to remotely view internal body structures. As such, endoscopes typically have lenses located at an insertion or distal end, and an ocular or viewer located at the proximal end of the instrument outside of the body. Often times, the viewer takes the form of a video monitor. A light source is provided at the distal end to illuminate the internal body area. Various tools are used to perform the procedures associated with the surgery, as viewed by the endoscope. These tools often include retractors, irrigators, snippers, lasers, and the like.

Each of these tools, along with the endoscope itself, must be inserted in a patient's body through a port, as noted above. A port is comprised of an incision in the patient's body into which a hollow, tubular cannula is inserted. The cannula then serves as a conduit for receiving and supporting the endoscopic instruments.

An endoscopic port is created and the cannula is simultaneously placed therein by means of a trocar. A trocar is a surgical instrument having a sharp triangular point that enters the body through a small surgical stab incision. The cannula fits over the trocar and enters the incision along with it, such that after the port is created and the trocar is removed, the cannula remains in place to define the endoscopic port. Typically, the cannula includes a headpiece which has a stopcock or other valve to control the flow of insufflation gas into and out of the patient's body. In addition, the external proximal ends of endoscopic instruments may be rested against the headpiece since they extend from the port during surgery. The weight of such instruments usually requires the use of a support device.

In a typical gallbladder surgery or cholecystectomy, as many as four to six ports must be made to accommodate the various endoscopic instruments needed to complete this procedure. Obviously, other types of endoscopic surgery will require more or fewer numbers of ports. Each port, including its associated cannula, must pass through the abdominal wall which includes the outer skin, a layer of fat, a layer of fascia or alternating muscle and fascia, and the peritoneum. The layers of fat and fascia may vary in thickness, depending upon the body location and whether the patient is asthenic or obese. The peritoneum is a strong, elastic membrane lining the walls of the abdominal cavity. Just below the peritoneum, however, lie several vital organs, such as the liver, stomach and intestines, and other sensitive tissues.

In cholecystectomies, as well as other types of endoscopic surgeries (appendectomies, etc.) a state of pneumoperitoneum is induced in the patient in order to provide an enlarged body cavity for manipulation of the endoscopic instruments and to avoid damage to internal organs and tissues. Thus, in pneumoperitoneum, the surgical area is insufflated with carbon dioxide. Insufflation is achieved initially with a so-called Veress needle which is a large needle used to puncture the patient for the introduction of gas. However, some risk arises from this process in that the needle may be penetrated too far into the body, thus injuring the patient. On the other hand, if the needle does not pass at least through the abdominal wall when insufflation is initiated, other serious risks arise.

Immediately after the initial insufflation with a Veress needle, a first endoscopic port is established via a trocar-guided cannula to permit internal visualization of the internal cavities. Thereafter, continued insufflation can occur through the cannula during surgery. As explained above, other endoscopic ports are necessary to accomplish the surgical procedure. Thus, the trocar, by providing a piercing guide for the cannula, which thereafter sustains pneumoperitoneum and defines a port for the surgical procedure itself, is critical to the success of endoscopic surgery.

However, the dangers of trocars are well recognized. In some cases, inadvertent visceral injury has occurred to vital organs through excessive trocar penetration. These dangers vary with the surgeon's experience, the dimensions of the trocar, and its site of insertion into the body cavity. Additional risks may arise from previous abdominal surgery, or peritonitis, in which adhesions may be responsible for complications associated with the insertion of the trocar and its associated cannula.

Thus, significant risks arise from the trocar establishment of endoscopic ports, especially the first port which is "blind." However, even with the aid of endoscopic vision, subsequent trocar insertion can also be a serious risk to the patient. This is due, in large part, to the combined toughness and elasticity of the abdominal wall which requires substantial manual force for trocar penetration. The built-up force, and subsequent momentum, which the surgeon develops in jabbing the trocar through the abdominal wall is difficult to reverse, thus leading, in some cases, to excessive penetration and injury. In order to limit the depth to which the trocar travels as it is pressed into the body, many surgeons use the ulnar border of the hand as a stop. Other surgeons press a finger along the axis of the cannula or trocar in order to limit the extent of travel. In both cases, however, the momentum of the insertion hand is simply transferred to these other limbs. This fact, combined with the flexibility of the abdominal wall which prevents it from successfully resisting penetration pressure, precludes these methods from offering an effective stop mechanism.

In order to reduce the risks of trocar usage, surgeons conventionally pinch a section of the skin with the hand not manipulating the trocar and lift it in the opposite vertical direction as the travel of the trocar. In other words, the abdominal wall is pulled upwardly with the intent of lifting the skin, fat, fascia, and peritoneum away from the vital organs below, thereby enlarging the void between the abdominal wall and such organs. This method is intended to provide a margin of error such that excessive penetration of the trocar will not reach the organs below the abdominal wall. This method, however, is also ineffective in many cases. First, it is difficult to get a good grip on the skin with the non-trocar hand, which is often the weaker hand of the surgeon. Secondly, the site of the finger pinch is, necessarily, somewhat removed from the site of the trocar insertion. Thus, only a portion or component of the lifting motion is transferred laterally to the exact location where the trocar is entering the body cavity. Thirdly, while the pinch method may be effective in asthenic persons, the thicker layers of fat in obese individuals render it highly unsatisfactory. Therefore, an improved method of trocar insertion is needed.

In light of the dangers of the above-described pinch method, specialized disposable trocars have recently been developed which are provided with spring loaded guards or shields for the sharp tip of the trocar. The shields are automatically deployed outwardly to cover the sharp tip of the trocar after abdominal wall penetration is achieved. Shield deployment, however, is sometimes delayed, and even a few milliseconds of delay can result in trocar injury. Furthermore, these trocars cost as much as several hundred dollars each and, since several must be used in a single endoscopic surgery, they result in greater expense. Thus, the use of shielded trocars is not a complete solution to this sensitive problem.

Another method for establishment of endoscopic ports, which does not require the use of a sharp trocar, is referred to as the "open laparoscopic" method. In accordance with this method, continuous visual control is maintained for insertion of a special open laparoscopic cannula. The key to this method is the use of an S-shaped retractor and Allis or Kocher type grasping forceps to laterally enlarge the initial incision and to lift the fascia. This procedure exposes the peritoneum and places it under tension so that it can be carefully pierced or incised. Although this method is relatively safe, it suffers from serious defects.

First, the procedure is lengthy and complicated, requiring a number of steps. In addition, insufflation pressure is lost due to the nature and length of time in which the port is open. Also, the port size is often larger than trocar induced ports, thus causing more discomfort and increasing recovery time for the patient. Thus, there is a need for a system of endoscopic port preparation which combines the advantages of a trocar without the attendant dangers.

Summary of the Invention

The present invention addresses and solves the problems of the prior art by providing a trocar facilitator which is securely positioned below the fascia, at the exact site of trocar insertion, which allows the surgeon to induce an upward force which counteracts the force of trocar penetration. Thus, not only is a lifting action induced which is opposite to the direction of travel of the trocar, but a state of counter-traction is generated which counteracts or neutralizes the dangerous downward momentum necessary for trocar penetration. Since the penetration motion can be much more carefully controlled, the risk of internal injury is greatly diminished or eliminated.

Another important advantage of this trocar facilitator is that it places the peritoneum in reverse or counter-tension against excessive trocar penetration. In other words, not only does the present facilitator lift the fascia and peritoneum away the vital organs below in order to create a margin for avoiding injury, it does so at the precise location of trocar penetration. Thus, the strength of the peritoneum is put to use by resisting excessive travel of the trocar. At the same time, because the peritoneum is placed in tension, it is somewhat easier to penetrate.

The trocar facilitator of the present invention can be adapted for use with conventional trocar systems which, as pointed out above, typically include a trocar for achieving peritoneal penetration, a cannula for forming the endoscopic port, and a cannula head piece for controlling certain functions in connection with the endoscopic port. However, due to its versatility, the trocar facilitator of the present invention can also be used compatibly with nonconventional, customized, or specially designed trocar systems, now existing or later developed. The present invention serves as a facilitator for promoting the safe use of a trocar, but also serves as a retractor for lifting the tissues of the patient upwardly as explained above. Moreover, in accordance with certain embodiments of the present invention, the trocar facilitator can achieve lateral traction at the site of the endoscopic port.

The present facilitator, once installed in the port location, serves as an anchor for the cannula or cannula head piece, thus providing support for endoscopic instruments and avoiding the need for other support devices and the like. Thus, the present facilitator comprises an anchor member which engages or grips the tissues of the patient near the site of the initial incision. The facilitator also comprises a lifting member, mounted on the anchor member, for providing the counter-traction described above. For example, such lifting member can comprise a handle or other device for manual lifting or retraction. If desired, the facilitator may also comprise a guide member for guiding the cannula and trocar into the incision for establishing the endoscopic port. Within this broad framework, the facilitator may be constructed in a wide variety of configurations. For example, the facilitator may be a single, integral piece. In another embodiment, the facilitator may be modular so as to permit it to break down into components (e.g., halves, thirds, etc.) so that it can be completely removed from the port site without disturbing the cannula of the trocar system.

In yet another embodiment, the anchor and lifting members are integral, forming, respectively, retractor blades and elongate handles for counter-traction. However, the guide member of this embodiment breaks down into components so that it can be separately installed or removed at the endoscopic site. In a further embodiment, the facilitator is provided with a distal cylindrical blade on the anchor member which grips the tissue of the patient in a rotary fashion, thus providing a secure anchor for the cannula of the trocar system. Thus, there is no need for any other support or instrument anchors since this embodiment of the facilitator provides a rigid and upright support which is strong enough to support various instruments, etc.

In another embodiment of the present invention, the trocar facilitator comprises a two-piece lifting member having handles and a removable corkscrew or rotary anchor member. Each half of the lifting member has a central portion in the shape of one-half of a cylinder. The two halves are brought together to form a cylindrical passageway used to guide the insertion of the trocar and cannula into the patient's body. The lifting member/guide piece is removably attached to the anchor member, which is configured in the shape of a corkscrew. The anchor member securely engages the fascial tissue in a rotary or corkscrew fashion, allowing enhanced counter-traction.

This embodiment of the present invention advantageously allows for improved gripping of tissue in a 360-degree circumference. As a result, increased counter-traction can be applied without damage to the tissue. The lateral retraction of the initial incision is minimized, thus a tight seal between the surrounding tissue and the trocar system is provided which helps prevent the loss of insufflation gas. In addition, the trocar facilitator of this embodiment can be fixed to the tissues, thus eliminating the need for external manual or structural support. The engagement of the corkscrew-like blade into the deep fascial layers serves as an anchor for vertically and securely holding the trocar system in place. This can be accomplished by removing the upper lifting member/guide piece from the lower anchor member and threadably engaging the cannula head piece thereon.

In this embodiment, the tip of the blade of the trocar facilitator is curved upward slightly, such that when the facilitator is positioned vertically in the patient's body, the point of the blade curves toward the surface of the body, thus lessening the risk of inadvertent puncture of vital organs below.

The trocar facilitator of the present invention can also advantageously be used to administer carbon dioxide gas to the patient to induce a state of pneumoperitoneum in the patient's body. In one embodiment, the gas is delivered through a passageway formed in the guide piece and the blade portion of the facilitator. Preferably, the passageway contains a hollow tube having a spring near its distal end. The distal end of the tube extends beyond the distal end of the blade when the spring is in its relaxed position. As the tip of the blade penetrates the tissue of the patient, sufficient resistance is encountered to compress the spring and push the tip of the tube behind the end of the blade. After the peritoneum is pierced, the resistance ceases and the spring relaxes, causing the tip of the tube to extend past the end of the blade. Gas may then be allowed to flow through the tube and into the abdominal cavity of the patient.

In other embodiments, the gas passage can be formed in the trocar itself. Because of the security with which the anchor member of the present facilitator can be mounted at the endoscopic port, the present invention also comprises a method and apparatus for suspending the patient's tissues in an extended position to permit endoscopic surgery with minimal insufflation. The present invention also comprises a novel method for forming an endoscopic port.

In summary, the trocar facilitator of the present invention can be constructed in a variety of configurations and be provided with a number of additional features, thus presenting substantial advantages over the trocar systems of the prior art.

BRIEF DESCRIPTION OF VARIOUS EMBODIMENTS OF THE DRAWINGS

FIG. 17 is a perspective view of a trocar facilitator of yet another, third embodiment of the present invention having distal teeth for securely gripping the fascial tissue.

FIG. 18 is an exploded view of a trocar system utilizing the trocar facilitator of FIG. 17 and a trocar, cannula, cannula head piece and rotary seal.

FIG. 23 is a partially cut-away side view of a fourth embodiment of the trocar facilitator of the present invention.

FIG. 24 is an exploded view of the trocar facilitator of FIG. 23, illustrating an anchor member and a two-piece lifting member.

DETAILED DESCRIPTION OF VARIOUS EMBODIMENTS OF THE INVENTION

Figure 1:
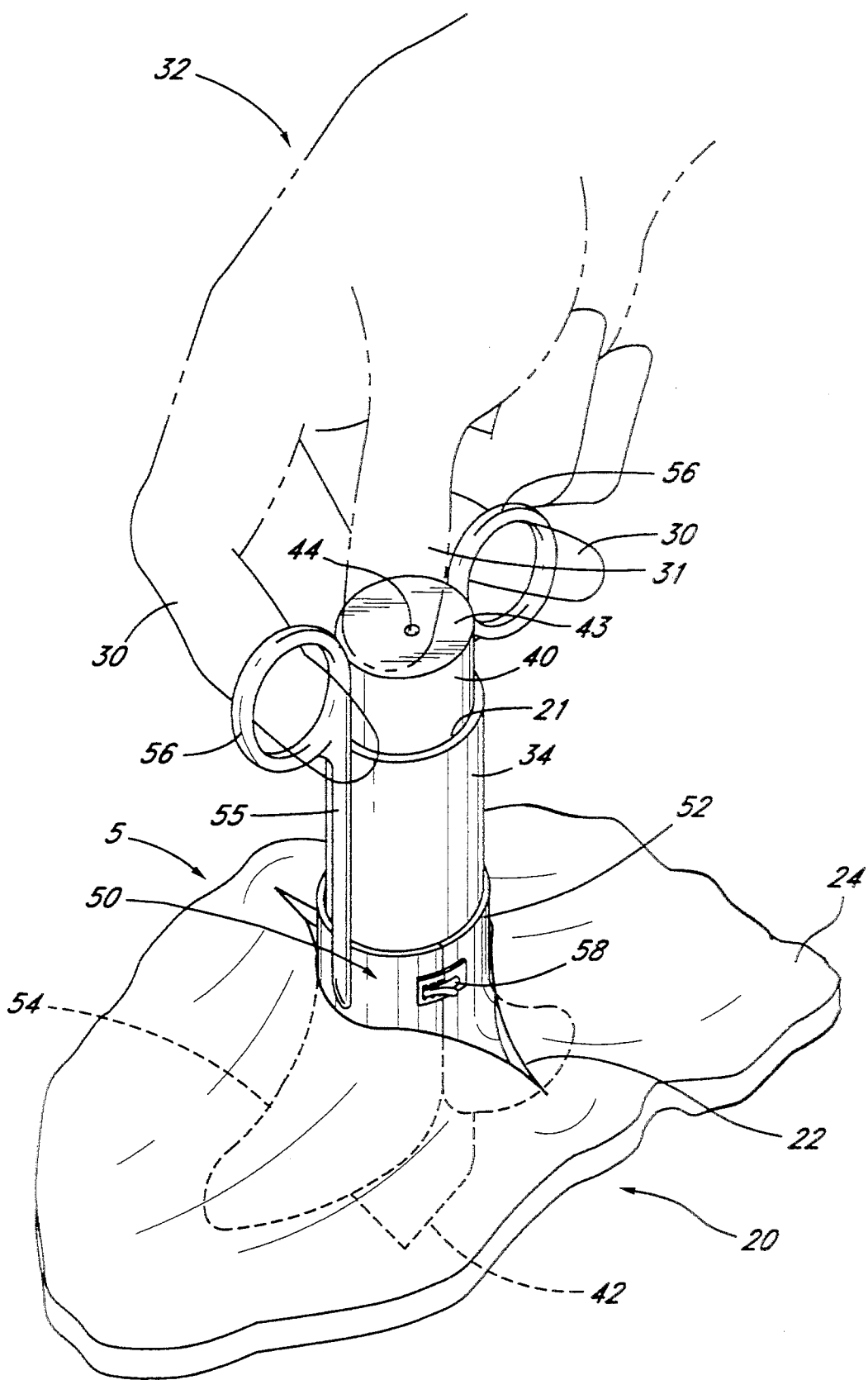
FIG. 1 is a perspective view of one embodiment of the trocar facilitator of the present invention illustrating the manner in which a single hand of a surgeon can induce an upward force which is counter or opposite to the direction of trocar penetration.

Referring to FIG. 1 there is shown a trocar system 20, including one embodiment of the trocar facilitator 5 of the present invention as inserted into a stab incision 22 in the patient preparatory to the formation of a port for endoscopic surgery. As noted above, however, it should be pointed out that the trocar facilitator of the present invention is not limited to any particular trocar system and can be adapted so as to be compatible with a wide variety of conventional or nonconventional trocars, now existing or hereinafter developed. In addition, a wide variety of trocar facilitator configurations is within the scope of the present invention.

The system 20 comprises the trocar 40, which is shown being pressed by the thumb 31 of the surgeon, its surrounding cannula 34 which will define the endoscopic port 21, and a trocar facilitator 50, which is retractable in an upward direction by the fingers 30 of the surgeon for providing counter-pressure to the penetration of the trocar 40. The sharp tip 42 of the trocar 40 is shown in dotted lines beneath the skin layer 24. It will be noted that the present invention is compatible with trocars of various dimension and diameters. At the external end 43 of the trocar 40 there is shown a small hole 44 which is the proximal opening of a trocar port 46 of the present invention, as is shown more completely in FIGS. 2-4. This trocar port 46 serves as a conduit for endoscopes or cannulas, as explained below in more detail.

The cannula 34 which surrounds the trocar 40 provides a conduit defining an endoscopic port 21. Through this endoscopic port 21, endoscopes and other instruments are inserted into the body cavity in order to achieve the surgical purpose. Continued insufflation of carbon dioxide gas may be sustained through the endoscopic port 21 during the procedure.

Still referring to FIG. 1, the facilitator 50 of the trocar system 20 is comprised of a guide portion 52, a pair of retractor blades 54 (shown in dotted lines beneath the surface of the patient's skin 24), and two handles 55 having finger loops 56 to receive the fingers 30 of the surgeon for imparting reverse motion to the system. Preferably, the facilitator 50 of FIG. 1 is constructed in two halves 51a,b (FIG. 3) which are mirror images of one another and which are capable of being joined and articulated about a latch 58. The manner of inserting and articulating these two halves 51a,b of the facilitator 50 are explained below in more detail and illustrated below in connection with FIGS. 5-10.

Figure 2:
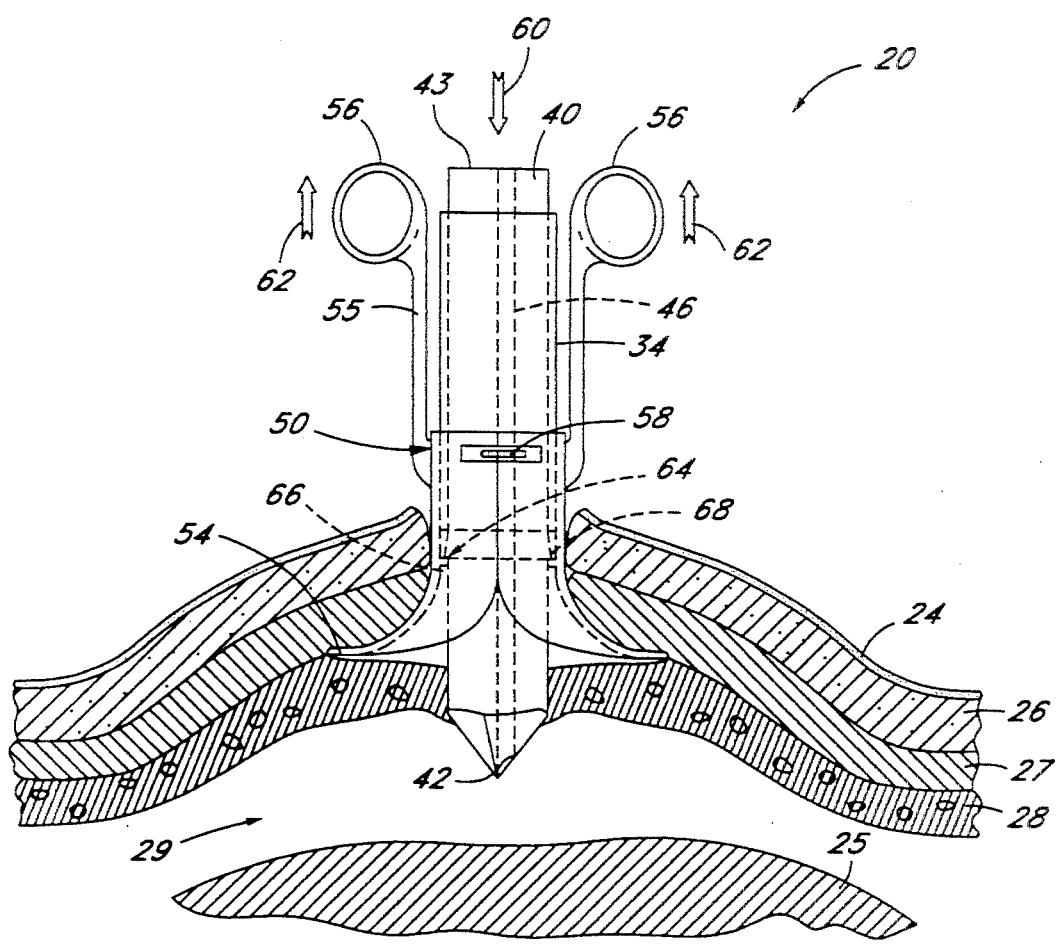
FIG. 2 is a cross-sectional view illustrating the penetration of the trocar into the body cavity as assisted by the counter-traction provided by the retractor blades of the trocar facilitator inserted into the lower portion of the fascial layer.

FIGS. 1 and 2 illustrate the preferred placement of the surgeon's hand 32 in connection with the trocar 40, and the forces imparted thereon. The thumb 31 of the hand 32 rests on the proximal end 43 of the trocar 40 for providing forceful downward penetration motion 60. At the same time, the fingers 30 of the hand 32 are inserted through the loops 56 of the facilitator handles 55 for providing an opposite upward force 62 on the system 20 to lift the abdominal wall of the patient's body away from vital organs 25 beneath and to minimize unnecessary downward trocar 40 penetration. In other words, it is important to note that the trocar system 20 of the present invention not only lifts the abdominal wall away from the vital organs 25 below, thereby creating a margin of safety 29, but also inherently generates a counter-motion or momentum which counteracts the downward penetration momentum of trocar 40 insertion. Thus, once penetration of the abdominal wall has been achieved, the downward momentum of penetration is simultaneously being counter-balanced and can be quickly stopped or even reversed. This presents a significant advantage over trocars of the prior art in which, once penetration was achieved, downward momentum was uncontrolled. Thus, the present trocar system 20 not only permits lifting, but also controls and counter balances downward penetration forces.

Trocar Facilitator of FIGS. 2-10

These important principles of the present invention are illustrated in FIG. 2 which is a partial cross-sectional view illustrating the placement of the trocar system 20 within the abdominal wall of the umbilicus region of a patient's body. The abdominal wall in the umbilicus region of humans encompasses the skin 24, fat 26, fascia 27, and peritoneum 28. In other regions of the body, muscle tissue is sandwiched between fascial tissues 27. The drawings showing a homogeneous fascial tissue layer 27 are considered representative of both regions. The peritoneum 28 is the strong, elastic membrane which protects the vital organs 25 below.

FIG. 2 illustrates the direction of the respective forces acting on the trocar system 20. The downward penetration motion 60 of the trocar 40 is counterbalanced or counteracted by the upward lifting forces 62 acting on the facilitator 50. Thus, the outer layers of tissue are lifted away from the vital organs 25 to provide a margin of error or safety 29 against excessive trocar 40 penetration. As shown in FIG. 2, therefor, the trocar 40 only slightly penetrates the peritoneum whereupon its downward momentum or force 60 is neutralized by the upward forces 62 acting on the facilitator 50. This upward force 62 is transferred to the trocar 40 by means of an annular stop device 64 which can take the form of an annular ledge 66 formed on the interior surface of the facilitator 50. This ledge 66 interferes with an annular ridge 68 formed on the exterior of the trocar 40. These components are shown in more detail and described in connection with FIGS. 3-4.

Once the trocar 40 has penetrated the peritoneum slightly, as shown in FIG. 2, an endoscope (not shown) can be inserted through the trocar port 46 in order to visualize the degree of penetration. Thereafter, the trocar 40 can be advanced carefully with the aid of endoscopic vision.

FIG. 2 illustrates the preferred placement of the facilitator blades 54 beneath the deeper fascial tissues 27. This positioning of the facilitator 50 improves its lifting capability even when thick layers of fat 26 are experienced, for example, in obese individuals.

Figure 3:
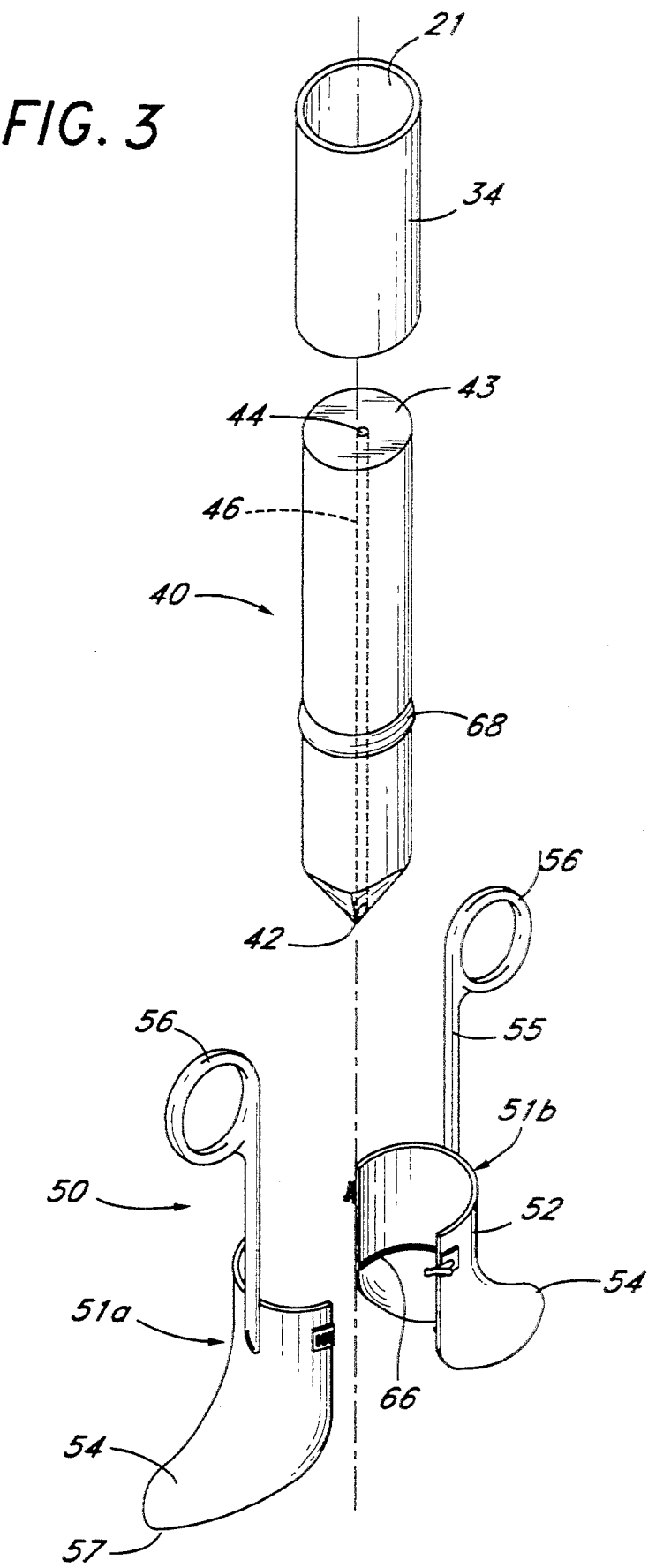
FIG. 3 is an exploded view of a trocar system including the trocar, the cannula and the trocar facilitator of the present invention having a two-piece retractor system.

FIG. 3 illustrates an exploded view of the trocar system 20, including the cannula 34, the trocar 40 itself and the two trocar facilitator halves 51a,b which together comprise the handle 55, guide portion 52 and blades 54 of the facilitator 50. As pointed out above, the cannula 34 is slidable over the trocar 40 and remains in place as the endoscopic port 21 for the insertion of endoscopes, instruments and the like. Its use and placement will be discussed below in more detail in connection with FIGS. 5-10.

Figure 4:
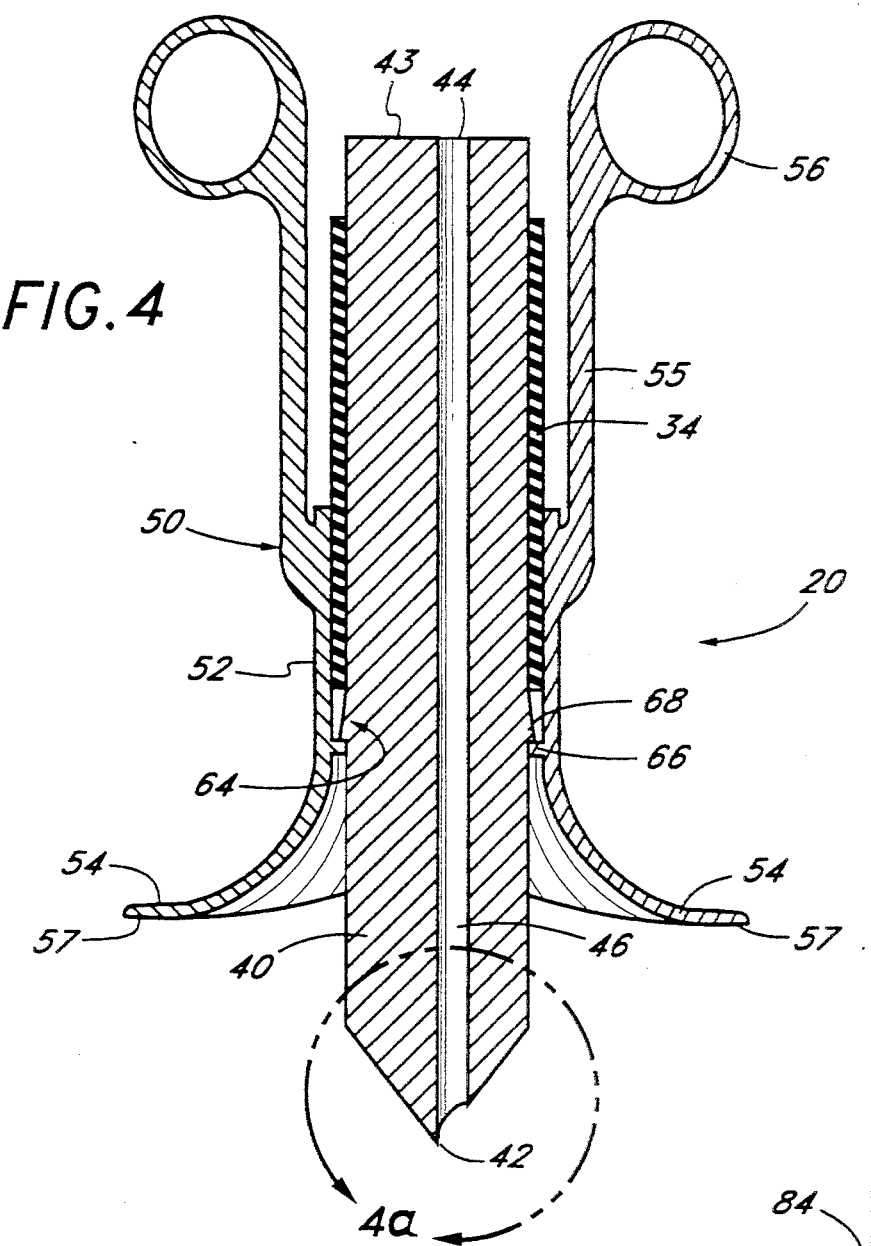
FIG. 4 is a cross-sectional view of one embodiment of the trocar facilitator of the present invention in its assembled state, and further illustrates a trocar port formed in the trocar itself.

The trocar 40 is as described above and includes a raised circumferential ridge 68 near its distal end 42 which comprises a portion of a stop device 64, illustrated in more detail in FIG. 4. Shown at the top of the trocar 40 is the proximal opening 44 of the trocar port 46, which is a cylindrical passage shown in dotted lines extending longitudinally through the entire length of the trocar 40 and exiting on one face of the tip 42 of the trocar.

The facilitator halves 51a,b are equipped with handles 55 having finger loops 56 for gripping and counter-traction, as explained above. When joined together, the two halves 51a,b comprise a guide portion 52 for receiving the trocar/cannula combination. The blades 54 extend approximately transversely to the axis of the trocar 40, and are insertable under the fascia 27 of the patient, as explained above in connection with FIG. 2. The facilitator halves 51a,b are joined together by a latch mechanism 58 which is releasable and can also permit, if desired, the two halves to articulate with respect to one another. On the interior surface of the guide portion 52 of the guide halves 51a,b is shown an annular ledge 66 which interferes with the annular ridge 68 on the trocar 40 to provide a stop device 64.

If desired, the blades 54 of this facilitator 50 can be made shorter and smaller so as to not cause enlargement of the incision 22, thereby inhibiting the escape of carbon dioxide gas used for insufflation.

FIG. 4 illustrates in cross section the trocar system 20 of FIGS. 2-3. It will be noted that the trocar 40 in FIG. 4 is in the same position as illustrated in FIG. 2, with the trocar being inserted to its maximum extent and having penetrated the peritoneum 28. Thus, FIG. 4 illustrates the ridge 68 surrounding the trocar 40 resting against the interior ledge 66 of the facilitator 50 in order to provide a stop device 64. This stop device 64, in combination with the counter-traction applied to the finger loops 56 of the facilitator 50, provide an effective impediment to excessive travel and penetration of the trocar 40. In addition, FIG. 4 illustrates the cannula 34 surrounding the trocar 40 and inserted into the guide portion 52 of the facilitator 50.

Figure 4A:
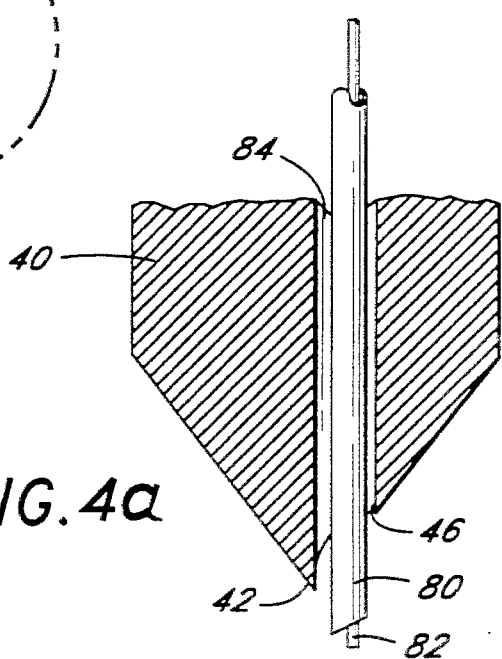
FIG. 4a is a detail view of the distal end of the trocar showing the trocar port and instruments therein.

FIG. 4 also illustrates the trocar port 46 which runs the length of the trocar 40 and allows the passage of endoscopic instruments. FIG. 4a is a close-up view of the distal opening of the trocar port 46 and illustrates a smaller auxiliary cannula 80 and interior endoscope 82 inserted therethrough. Thus, it will be noted from FIG. 4a that even with these instruments inserted in the trocar port 46, there is still an annulus 84 which allows the passage of insufflation gas. An important advantage of the present invention is that the trocar system 20 can eliminate the use of a Veress needle (not shown) for insufflation purposes, which itself can be dangerous. In other words, the surgeon can inadvertently pierce or penetrate a vital organ 25 with the Veress needle, thus causing injury to the patient. On the other hand, if the needle is not inserted deep enough, past the peritoneum, before insufflation begins, the state of pneumo-omentum occurs, which can also be injurious to the patient. With the trocar system 20 of the present invention, once the surgeon believes that penetration through the peritoneum 28 has been achieved, an auxiliary cannula 80 and endoscope 82 combination can be inserted through the trocar port 46 to visualize the extent of penetration of the trocar 40. If sufficient penetration has been achieved, initial insufflation can begin through the trocar port 46. Otherwise, continued trocar 40 penetration can be safely accomplished with visualization from the endoscope 82, as shown in FIG. 4a.

Another advantage realized by the trocar port 46 is the ability to insert and retract the trocar 40 from the endoscopic port 21 without forcing gas into the patient or suctioning matter from the patient. In other words, with a tight seal between a conventional solid trocar and cannula, the trocar acts substantially as a piston. The trocar port 46 of the present invention, however, provides a release means for any pressure differential between the body cavity and the exterior of the patient caused by trocar 40 movement.

FIGS. 5-10 illustrate the method of the present invention and the manner of using the trocar facilitator 50 described above in connection with FIGS. 2-4.

Figure 5:
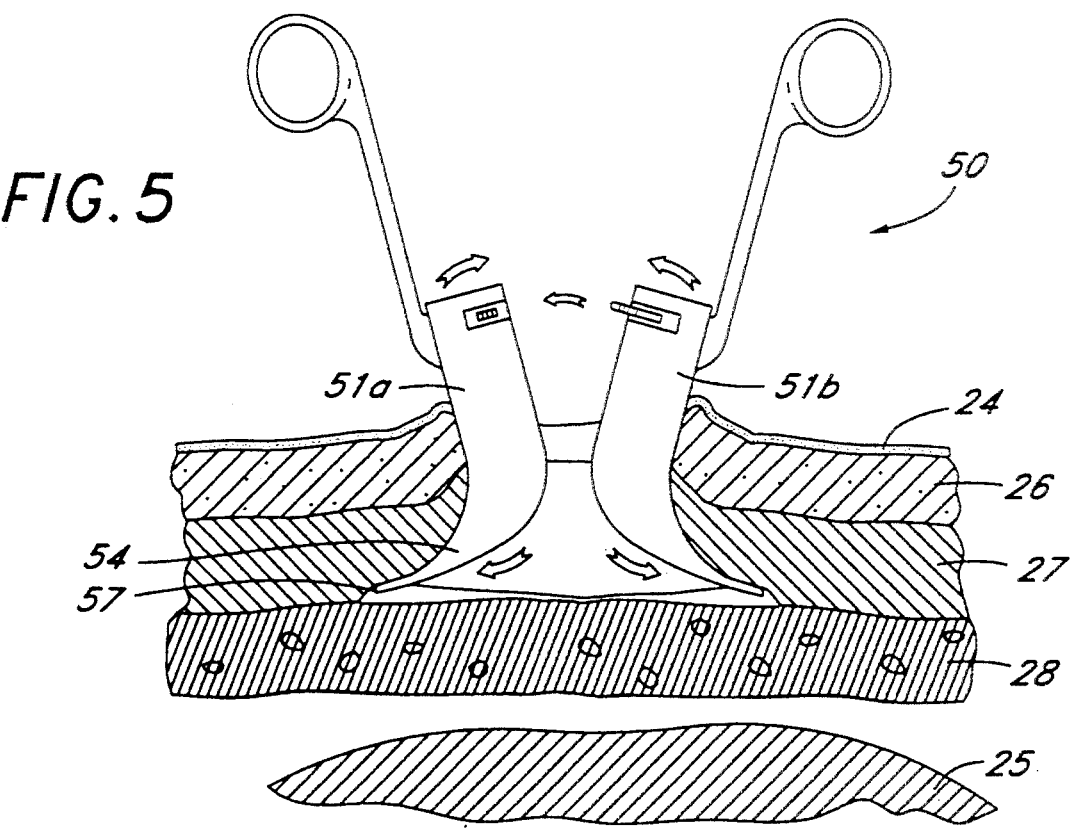
FIGS. 5-10 are partial cross-sectional views illustrating the method of using the trocar facilitator of the present invention, including the manner of its use.

FIG. 5 illustrates the manner in which the facilitator 50 of the trocar system 20 is introduced into the patient. First, a deep incision 22 (FIG. 1) is made in the patient's skin 24 and fat layer 26 as the first step in the generation of an endoscopic port 21. This incision 22 comprises essentially a short stab incision which preferably reaches the deeper fascial tissue 27. If necessary, the walls of the incision 22 may be laterally retracted to aid in the insertion of the trocar system 20. One of the facilitator halves 51a is then positioned near this incision 22 in a substantially horizontal manner such that the longitudinal axis of the facilitator half is parallel to the patient's skin 24 at the location of the incision. In this configuration, the blade 54 of the facilitator half 51a is substantially transverse to the patient's skin 24 and its distal end 57 is introduced into the incision 22 in a downward movement. The blade 54 of the facilitator half 51a is inserted as deeply as necessary into the incision 22. The facilitator half 51a is then rotated approximately 90° in a clockwise direction, as indicated by the arrows in the left-hand side of FIG. 5. This rotation brings the facilitator half 51a into a position which is essentially perpendicular to the patient's skin 24 at the location of the incision 22 and causes the tip 57 of the blade 54 to penetrate laterally and beneath the fascia 27 until an erect position is assumed, as shown in FIG. 6.

A similar motion is performed with respect to the opposite facilitator half 51b except that the rotation is counter-clockwise, as shown by the arrows on the right side of FIG. 5. When both facilitator halves 51a,b are brought to an erect position, they may be brought together in the direction of the arrows shown in FIG. 6 and interconnected by means of the latch 58.

Figure 7:
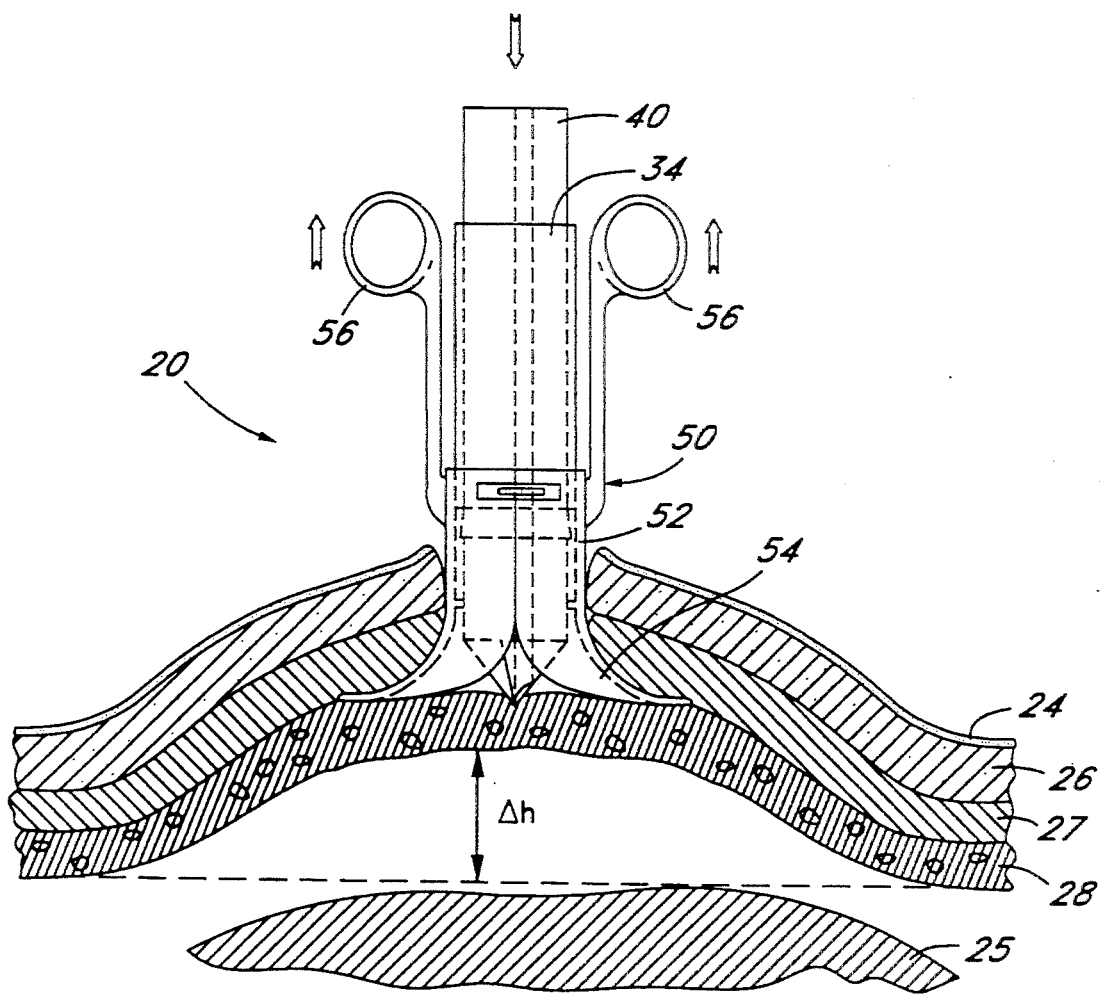

The advantage of this method of insertion of the facilitator halves 51a,b is that it minimizes the size necessary for the incision 22 and maintains a smaller incision opening during installation. Moreover, the blades 54 of the facilitator 50 are inserted securely beneath the fascia 27 in accordance with this method. Therefore, improved counter-traction can be obtained by the blades 54, as explained above in more detail. With the facilitator halves 51a,b secured together as shown in FIG. 7, they provide a secure and erect guide portion 52 for the trocar/cannula combination to be inserted therethrough, the facilitator 50 is self-supporting and can hold other instruments, including the cannula 34 and the trocar 40 without having to be supported by the surgeon's hands. This allows the surgeon to accomplish other procedures, thereby shortening the time for this endoscopic port procedure.

Figure 6:
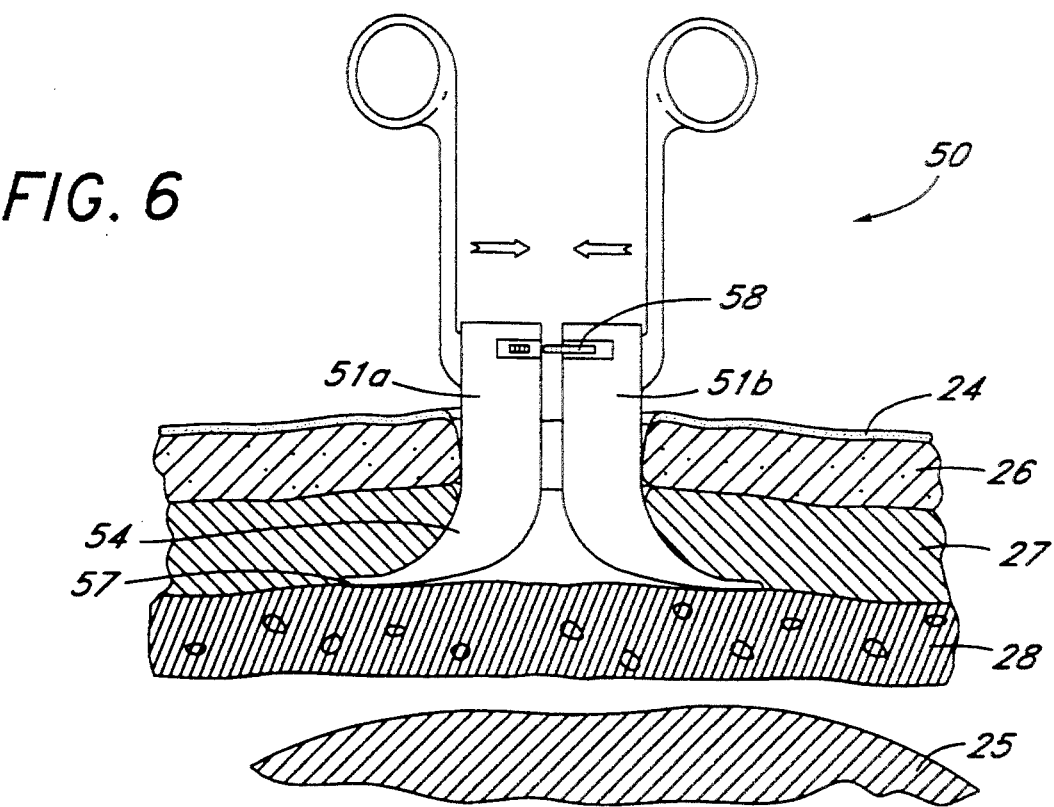
Figure 8:
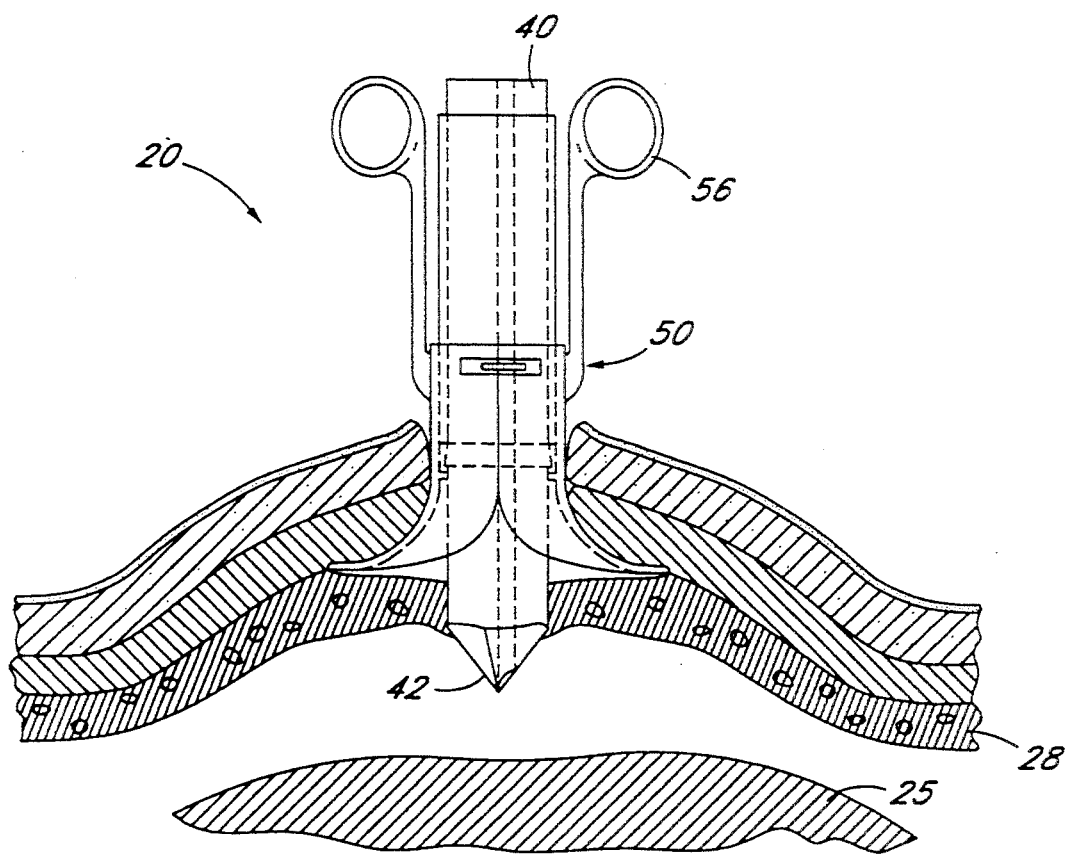

It will be noted in FIGS. 5 and 6, the close proximity of the vital organs 25 just beneath the peritoneum 28. FIG. 7 illustrates, in a manner similar to FIG. 2, the use of the trocar facilitator of the present invention to retract the peritoneum 28 and other tissue layers upwardly away from the vital organs 25 prior to the penetration of the trocar 40. Thus, it will be noted that once the trocar 40 and cannula 34 are inserted into the facilitator 50, a retraction of approximately Ah can be achieved in accordance with the device and method described above. Once this retraction has been achieved, penetration of the trocar 40 can safely begin. The counter-traction, as achieved by the handle finger loops 56 and manual force applied thereto in the direction of the arrows shown in FIG. 7, tends to neutralize the downward momentum of the trocar's penetration, thus further insulating the vital organs 25 from injury. Finally, as shown in FIG. 8, once the trocar 40 has completely penetrated the peritoneum 28, forward progress of the trocar 40 is easy to control due to the effect of counter-traction and the tension placed upon the peritoneum 28 at the point of penetration by the counter-traction itself. If it is desirable and necessary to continue penetration of the trocar 40, that can be safely accomplished with the assistance of endoscopic visualization in the manner described above in connection with FIG. 4a.

Figure 9:
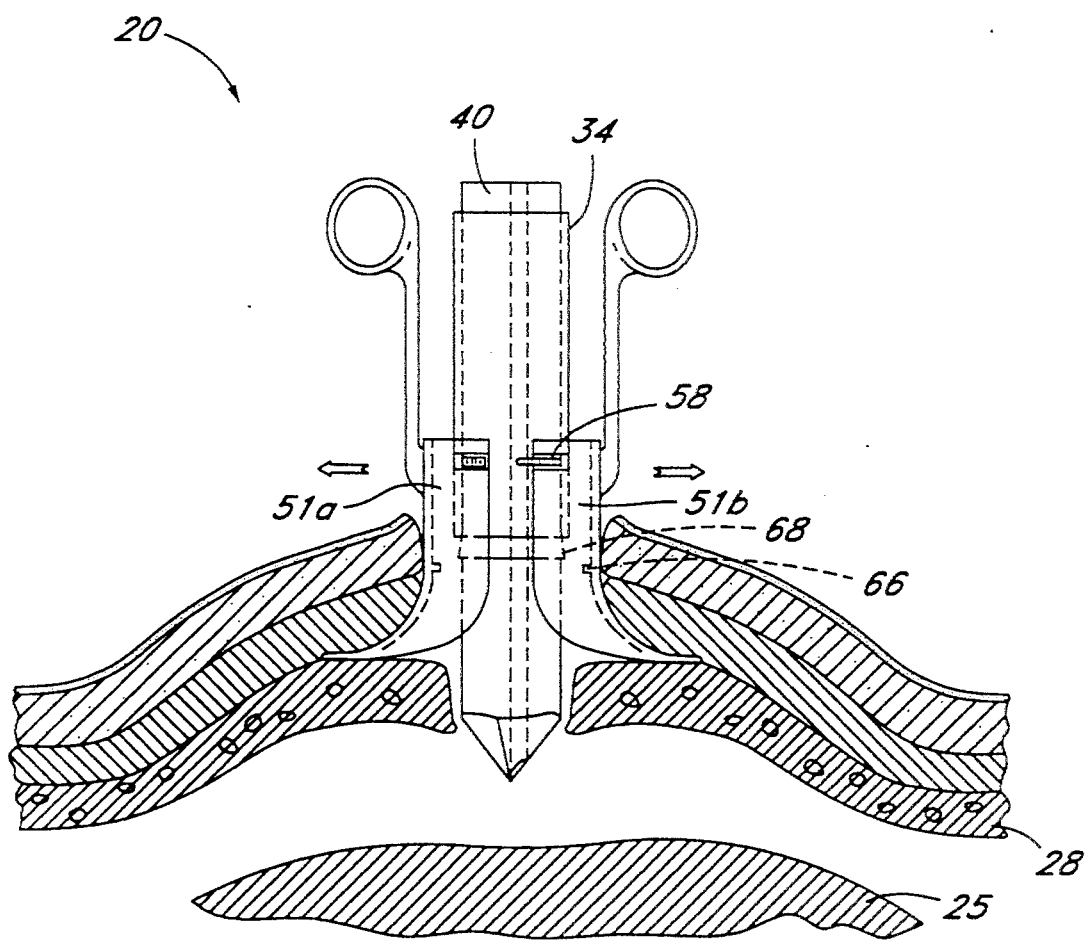
Figure 10:
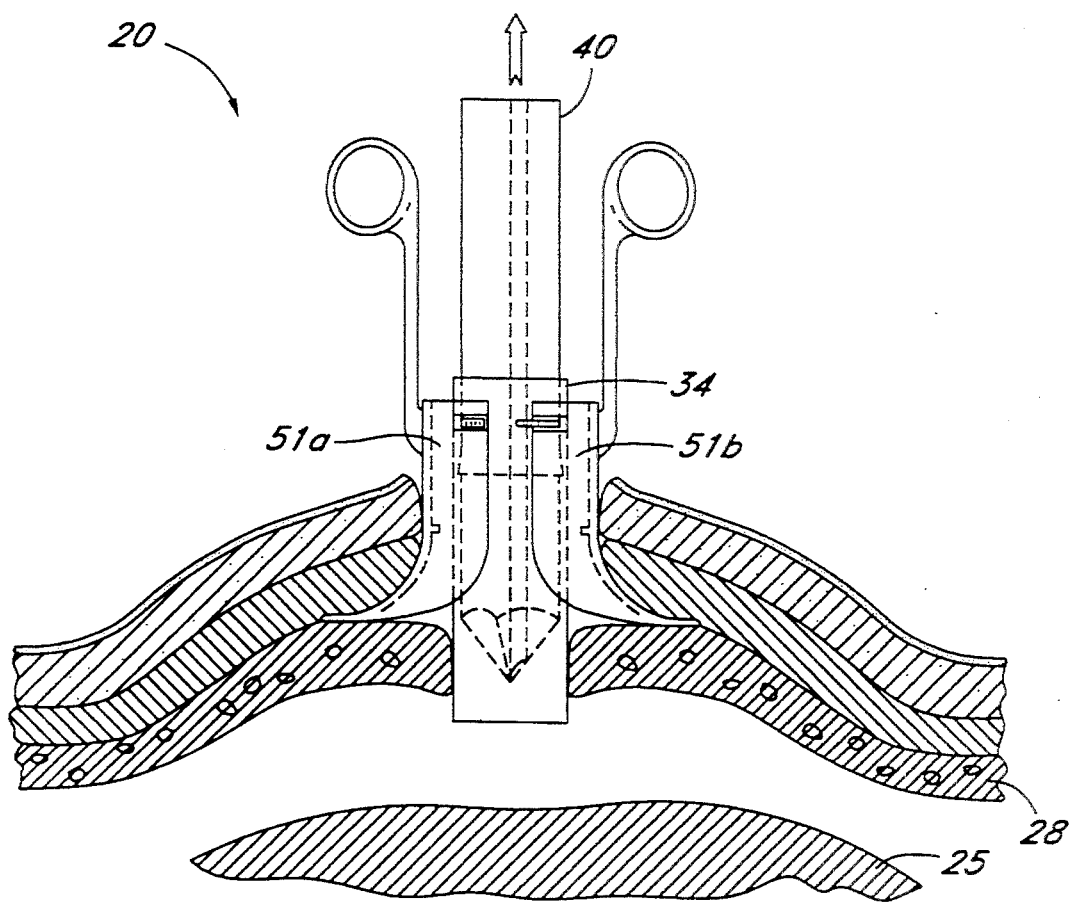

FIGS. 9 and 10 illustrate the manner in which the cannula 34 of the trocar system 20 can be installed in place in order to form the endoscopic port 21. The facilitator halves 51a,b of the trocar system 20 are first separated slightly, in a manner similar to FIG. 6, by disconnecting the latch 58. This slight separation allows the cannula 34 to pass downward over the ridge 68 on the trocar 40 and past the interior ledge 66 of the facilitator halves 51a,b. Thus, the cannula 34 can be advanced downward through the hole in the peritoneum 28 formed by the trocar 40, using the trocar 40 as a guide. Once the cannula 34 is in place through the peritoneum 28, as shown in FIG. 10, the trocar 40 can be removed so as to allow the passage of endoscopic instrumentation. If desired, the facilitator halves 51a,b can be once again connected to provide a rigid vertical support for the cannula 34 or for other instruments that may be placed therethrough.

Trocar Facilitator of FIGS. 11-16

Figure 11:
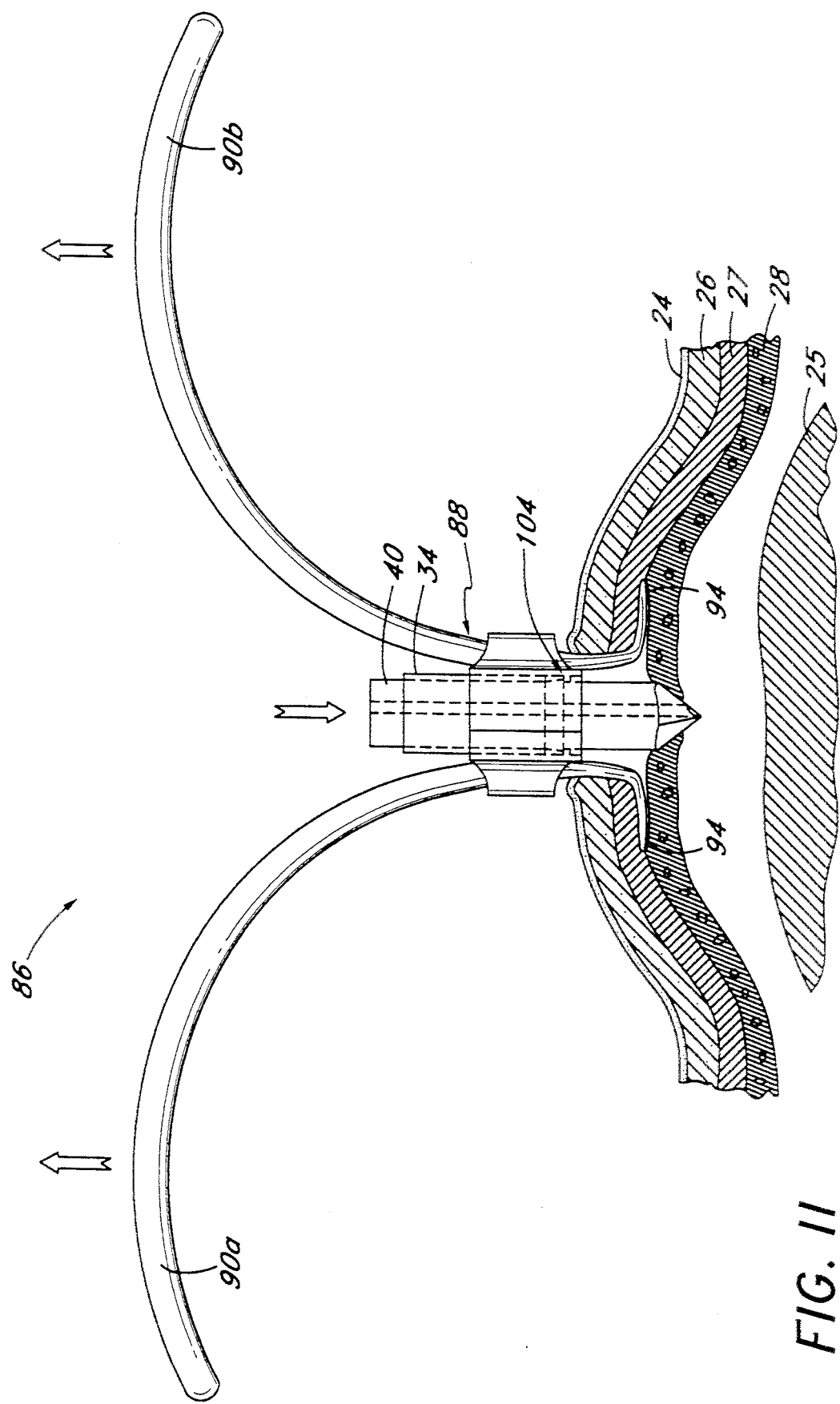
FIG. 11 is a partial cross-sectional view illustrating another embodiment of the trocar facilitator of the present invention using larger handles for counter-traction which are suitable for two-handed use.

FIG. 11 illustrates a trocar system 86 in which the trocar facilitator 88 of the present invention is provided with large arcuate handles 90a,b, the distal ends of which form the blades 94 for insertion under the fascia 27. With this facilitator 88 configuration, greater counter-traction can be achieved because the lifting force, as shown by the arrows in FIG. 11, is applied directly to the blades 94 and to the fascia 27. If desired, retraction in the reverse direction can be achieved with both hands of the surgeon while trocar penetration is achieved with one of the thumbs. If desirable, or necessary, an assisting surgeon may retract the handles 90a,b while the head surgeon manipulates the trocar 40 down into the peritoneum 28. Thus, the trocar 40 and cannula 34 are utilized in connection with the facilitator 88 of FIG. 11 in a manner similar to that as described above for the trocar facilitator 50 of FIGS. 2-10.

It will be noted that the blades 94 formed on the end of the facilitator handles 90a,b are somewhat shorter and more angular than the blades 54 of the previous embodiment. This configuration allows for a more secure grip by the blades 94 and handles 90a,b beneath the deep fascial layer 27 in order to improve counter-traction. This is an important advantage since, in some patients, the layer of subcutaneous fat 26 can measure up to 10-20 centimeters.

The two halves 96a,b which form the trocar guide 98 of this embodiment are also configured somewhat differently, as illustrated in detail in FIGS. 12-16. In this embodiment, each guide half 96a,b is slidably mounted on its respective handle 90a,b by means of a channel 100. Thus, either guide half 96a,b can be slid up and away from the incision site during installation of the trocar system 86. Specifically, FIGS. 12-15 illustrate the method associated with the present invention and the manner of use of this particular trocar facilitator 88 within the trocar system 86.

Figure 12:
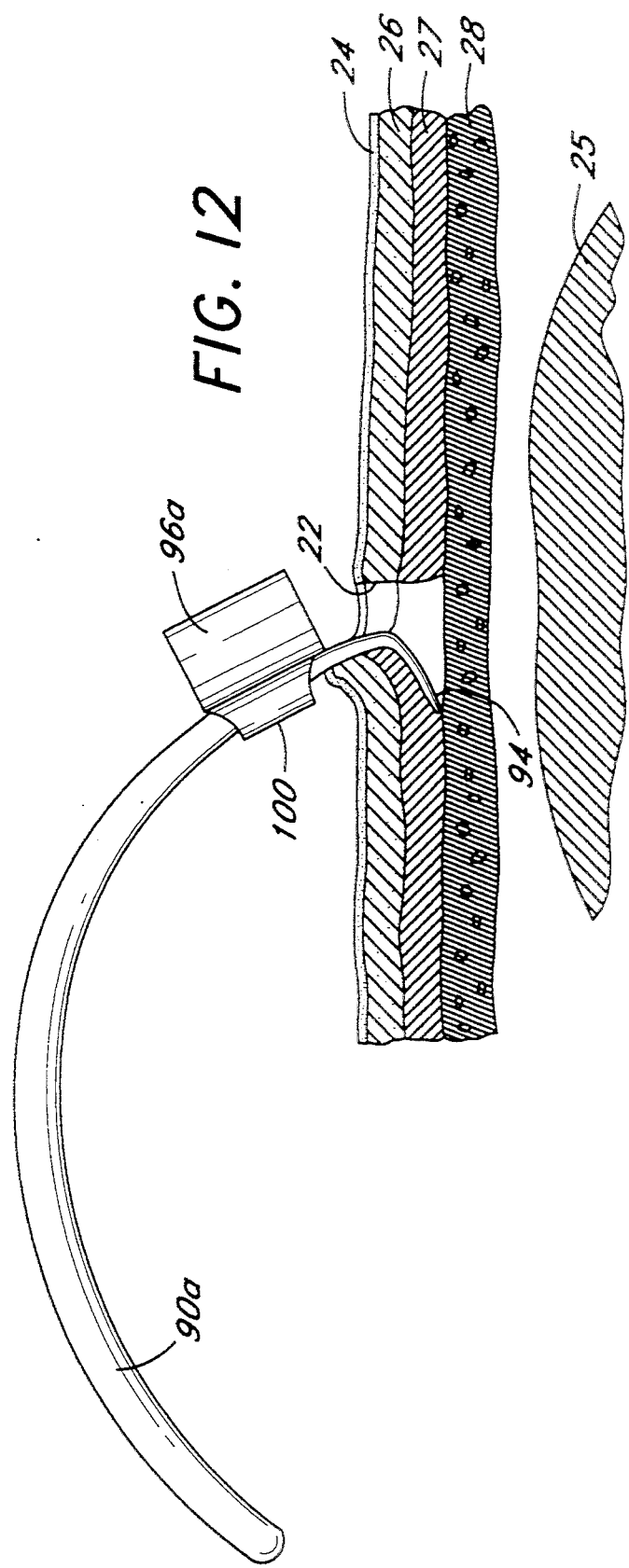
FIGS. 12-15 illustrate the manner and method of using the trocar facilitator of the second embodiment of the present invention.
Figure 13:
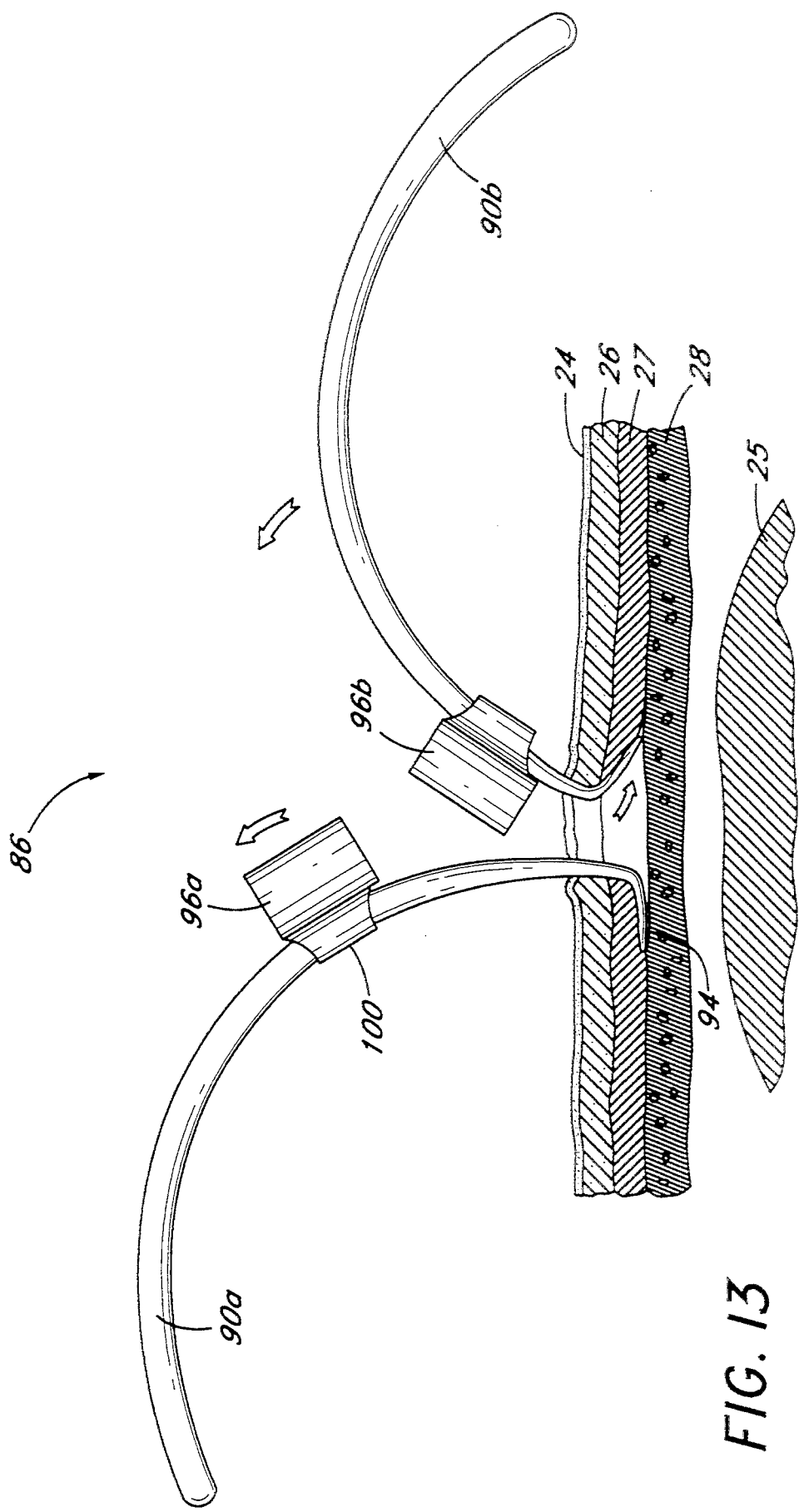

Referring to FIG. 12, the first incision 22 causes some relaxation of the skin 24, fat 26, and fascial layer 27, causing them to part slightly. However, if necessary, the incision 22 can be retracted slightly in a lateral direction in order to facilitate introduction of the trocar facilitator 88. In a manner similar to that described above in connection with the trocar facilitator 50 of FIGS. 2-10, the blade 94 of one of the handles 90a of the trocar facilitator 88 of FIG. 12 is introduced into the incision 22 in a direction substantially transverse to the patient's skin 24. The handle 90a is then rotated approximately 90° in a clockwise direction such that the facilitator blade 94 assumes the position shown in FIG. 13. Thus, the blade 94 is inserted beneath the fascial layer 27 for secure counter-traction. It will also be noted from FIG. 13 that the associated guide half 96a can be slid upward so as to not interfere with the installation of the guide half 96b on the opposite handle 90b. The second handle 90b is installed in a similar manner except that rotation is in a counter-clockwise direction, as shown by the arrow in FIG. 13.

Figure 14:
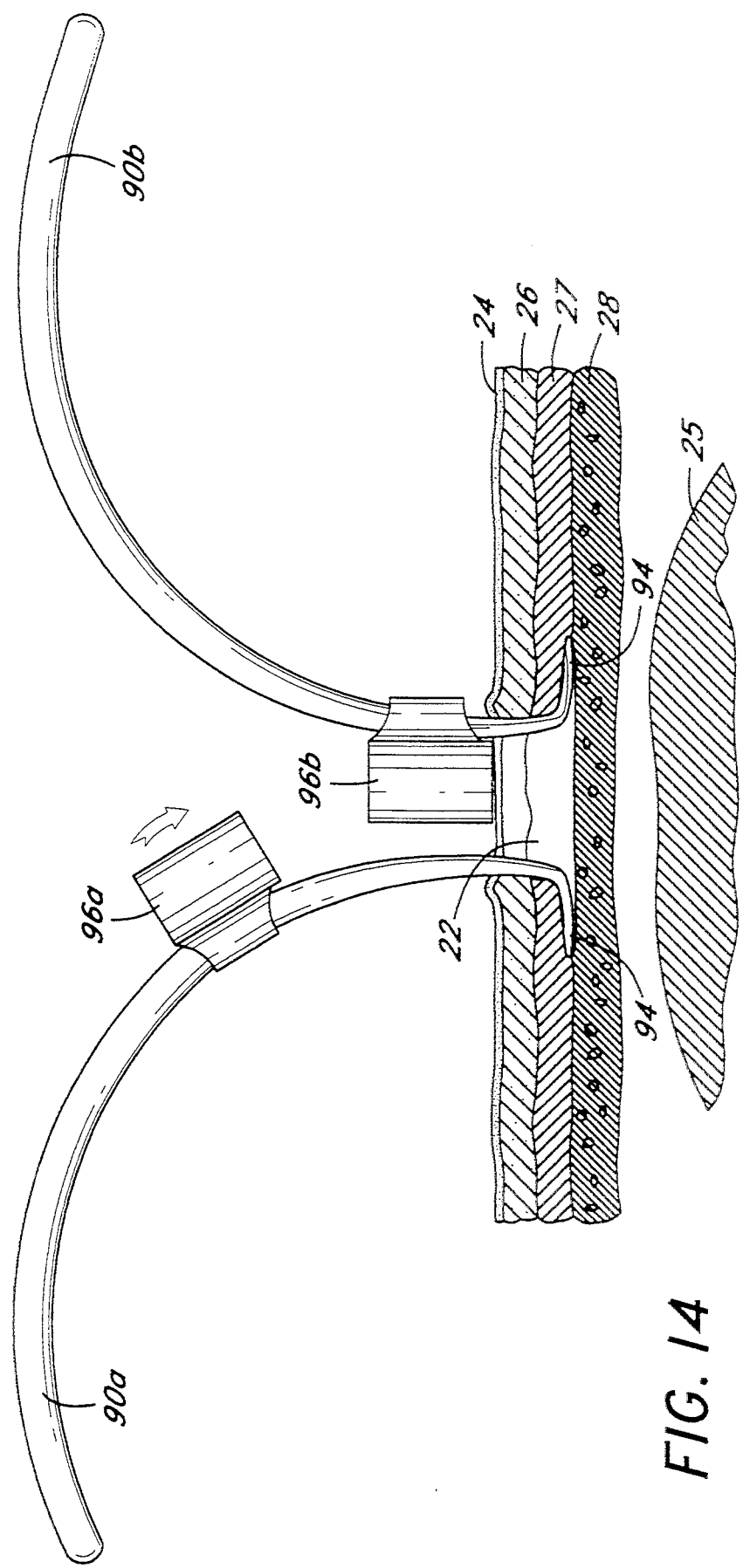
Figure 15:
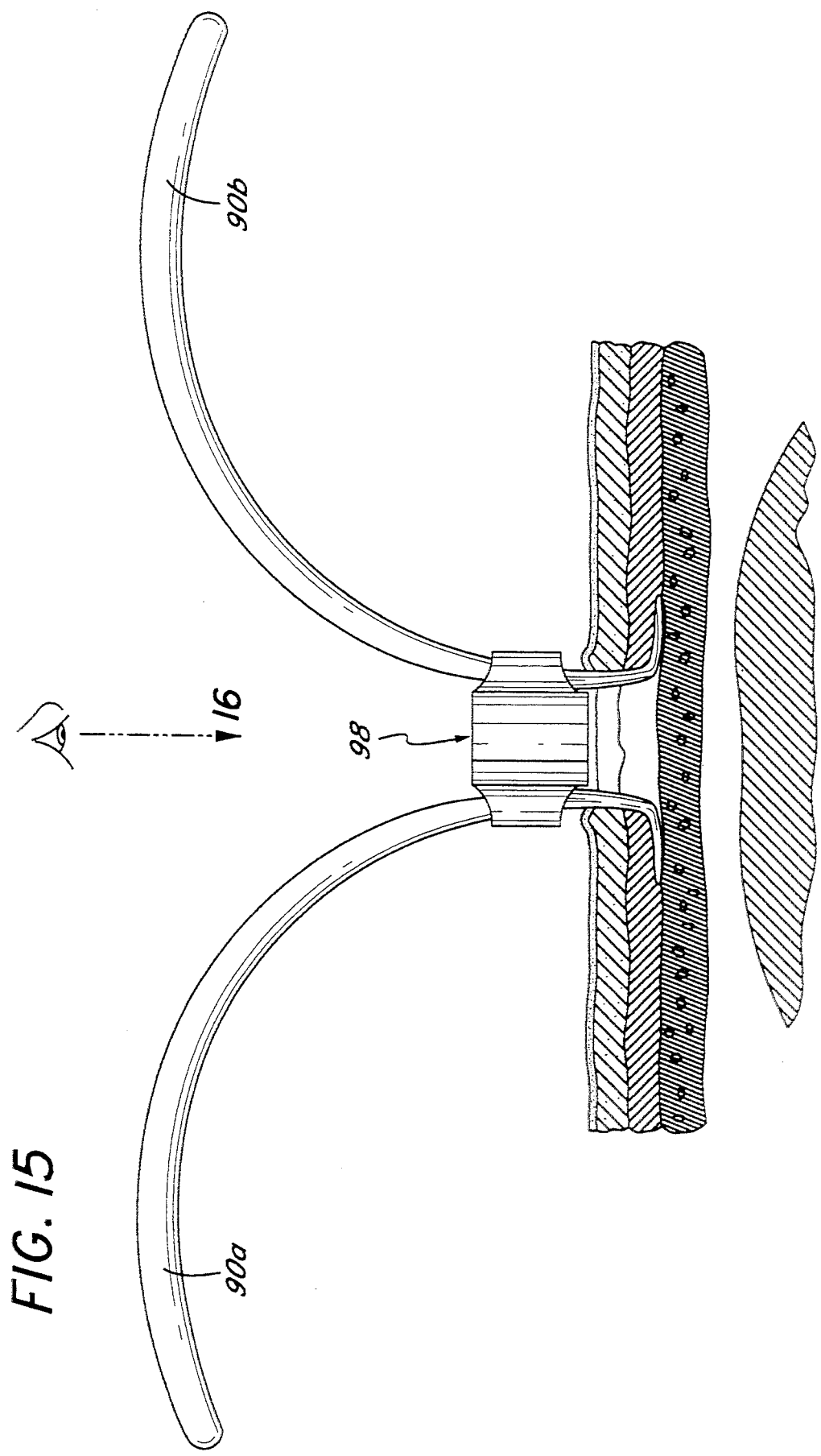

FIG. 14 illustrates the positions of the handles 90a,b once they are installed in the incision 22. The first guide half 96a can then be slid downwardly into a nesting, mating relationship with the second guide half 96b to form a complete cylindrical guide 98, as shown in FIG. 15. The completed guide 98 can then receive the trocar/cannula combination, as illustrated in FIG. 11.

Figure 16:
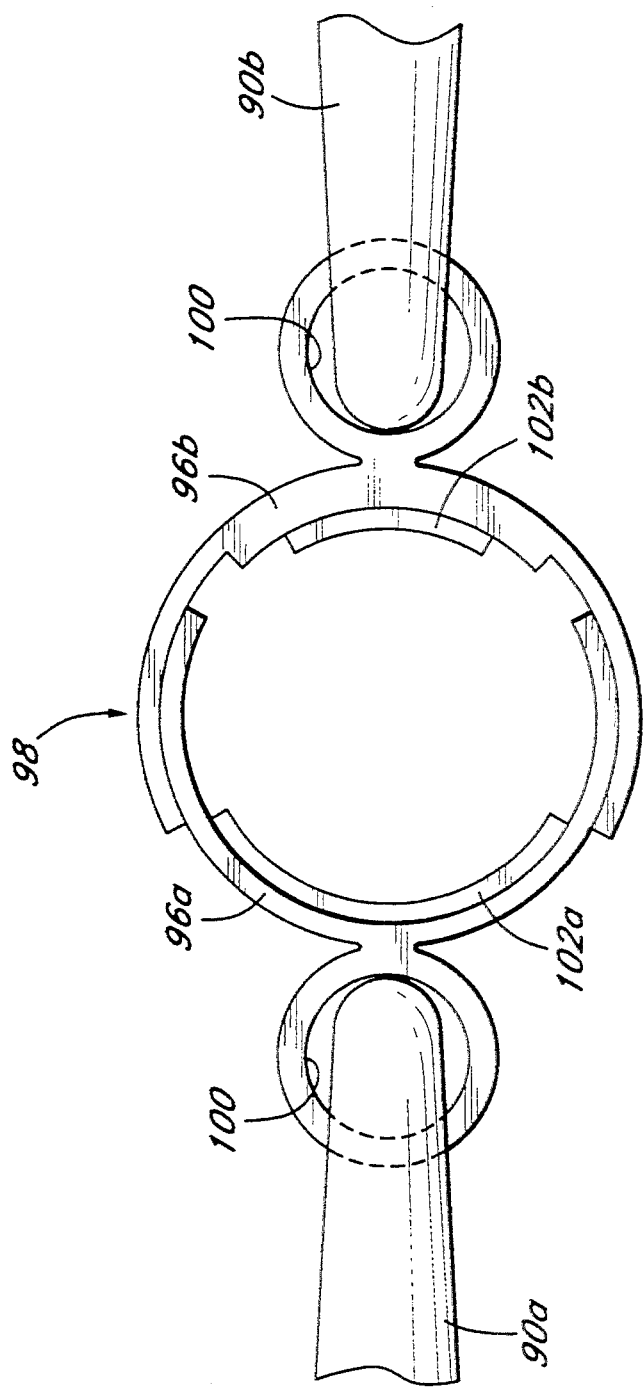
FIG. 16 is a top view of the second embodiment of the trocar facilitator of FIGS. 11-15.

FIG. 16 illustrates a top view of the trocar system 86, including the completed guide 98 and the overlapping ends of each respective guide half 96a,b. Also illustrated are interior ledges 102a,b combining to act as a trocar stop device 104 (seen in FIG. 11), in a similar manner to the embodiment shown in FIGS. 2-10. Mounted on the exterior of the guide halves 96a,b are the channels 100 which slidably receive the respective guide handles 90a,b , as explained above.

Thus, the trocar facilitator 88 of this embodiment can be efficiently utilized to maximize counter-traction.

Trocar Facilitator of FIGS. 17-21

In some cases, the trocar systems 20, 86 of the previous embodiments may not provide a sufficient engagement of the tissue by the anchor member of the trocar facilitator to achieve the degree of retraction or counter-traction necessary. For example, the fat layer 26 of the patient may obscure the visualization of the fascia 27 deep in the incision 22 and prevent the correct placement of the blades of the trocar guide. In addition, in order to avoid the loss of insufflation gas around the site of facilitator insertion, it may be desirable to use a gripping configuration which will not tend to enlarge the incision 22 to any degree beyond only that which is necessary to form the endoscopic port.

Accordingly, another trocar system 120, including a trocar facilitator 122 of a third embodiment, is illustrated in FIGS. 17-21. Referring first to FIG. 17, there is shown the trocar facilitator 122 of this embodiment which comprises a complete cylinder, or guide portion 124, having a pair of opposed transverse handles 126 for providing counter-traction. At the distal end 123 of the facilitator 122, there is shown a pair of sharp pointed teeth grippers 128 constructed in rotary or corkscrew fashion. As will become apparent below, these grippers 128 are designed to bore into the fascial tissue 27 in order to provide a secure gripping force for the facilitator 122. In this manner, sufficient counter-traction force can be applied to the incision site without excessive enlargement of the incision 22 and without the need for deep fascial visualization.

FIG. 18 illustrates the complete trocar system 120, including the trocar facilitator 122 described above, the cannula 140 including its associated integral head piece 142 at the proximal end, and the trocar 150 extending through the cannula. Also shown near the distal end 141 of the cannula 140 is a rotary seal 144 having exterior threads 145 which prevents the loss of insufflation gas around the cannula 140 at the site of penetration.

In somewhat conventional fashion, as shown in FIG. 18, the head piece 142 contains a flapper valve 146 for preventing the loss of insufflation gas. However, this valve 146 allows for the passage of the trocar 150 down through the head piece 142 and the cannula 140, such that the tip 152 of the trocar 150 is exposed at the distal end 141 of the cannula 140. Thus, once the trocar 150 has penetrated the peritoneum 28 in order to form the endoscopic port, the trocar can be removed, leaving the cannula 140 and head piece 142 in place. The valve 146 prevents the loss of insufflation gas but allows the passage of other endoscopic instruments therethrough. The method of this invention and the manner of use of the trocar facilitator 122 of this embodiment is illustrated in connection with FIGS. 19 and 20.

Figure 19:
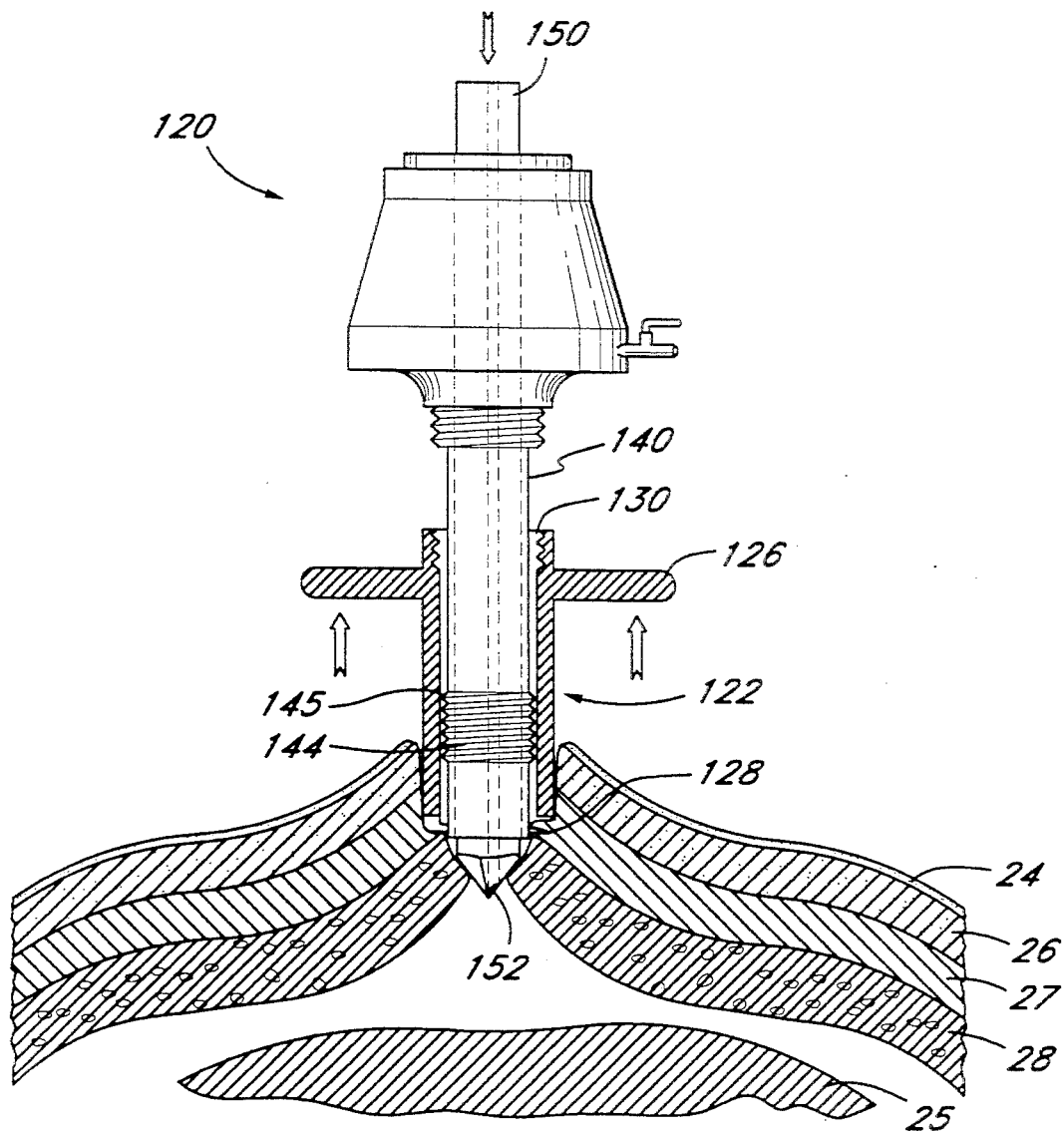
FIGS. 19-21 illustrate the manner and method of using the trocar facilitator of the third embodiment of the present invention.

Referring first to FIG. 19, after the incision 22 is made, the facilitator 122 alone is inserted into the incision 22 in order to initiate the counter-traction process. Typically, retraction of the incision 22 is not necessary to allow introduction of the facilitator 122; however, if desired, slight retraction of the incision can be accomplished in order to facilitate the passage of the facilitator 122 into the deeper fascial tissues 27. An important advantage of the trocar facilitator 122 of this embodiment, however, is the fact that actual visualization of the fascial tissues 27 is not necessary. Once the facilitator 122 has been securely seated in the incision 22, it can simply be rotated by means of the handles 126 approximately one-quarter or one-half turn in order to cause the rotary grippers 128 to bite or securely grip the deep fascial tissues 27 in the incision. Thus, as shown in FIG. 19, counter-traction can then be applied to the handles 126 in order to lift the tissue layers of the patient away from the vital organs 25 beneath. At the same time, the cannula 140 and trocar 150 combination can be passed down through the facilitator 122, in the same manner as explained above, and penetration of the trocar through the peritoneum 28 can be accomplished. In this embodiment, the rotary seal 144 provides a form of a stop device because of the threads 145 located on the exterior thereof. In other words, the threads 145 interfere with the tissues on the side walls of the incision 22 and provide a resistance to deeper penetration. This advantage, combined with effective countertraction, protects the vital organs 25 beneath the tip 152 of the trocar 150.

Figure 20:
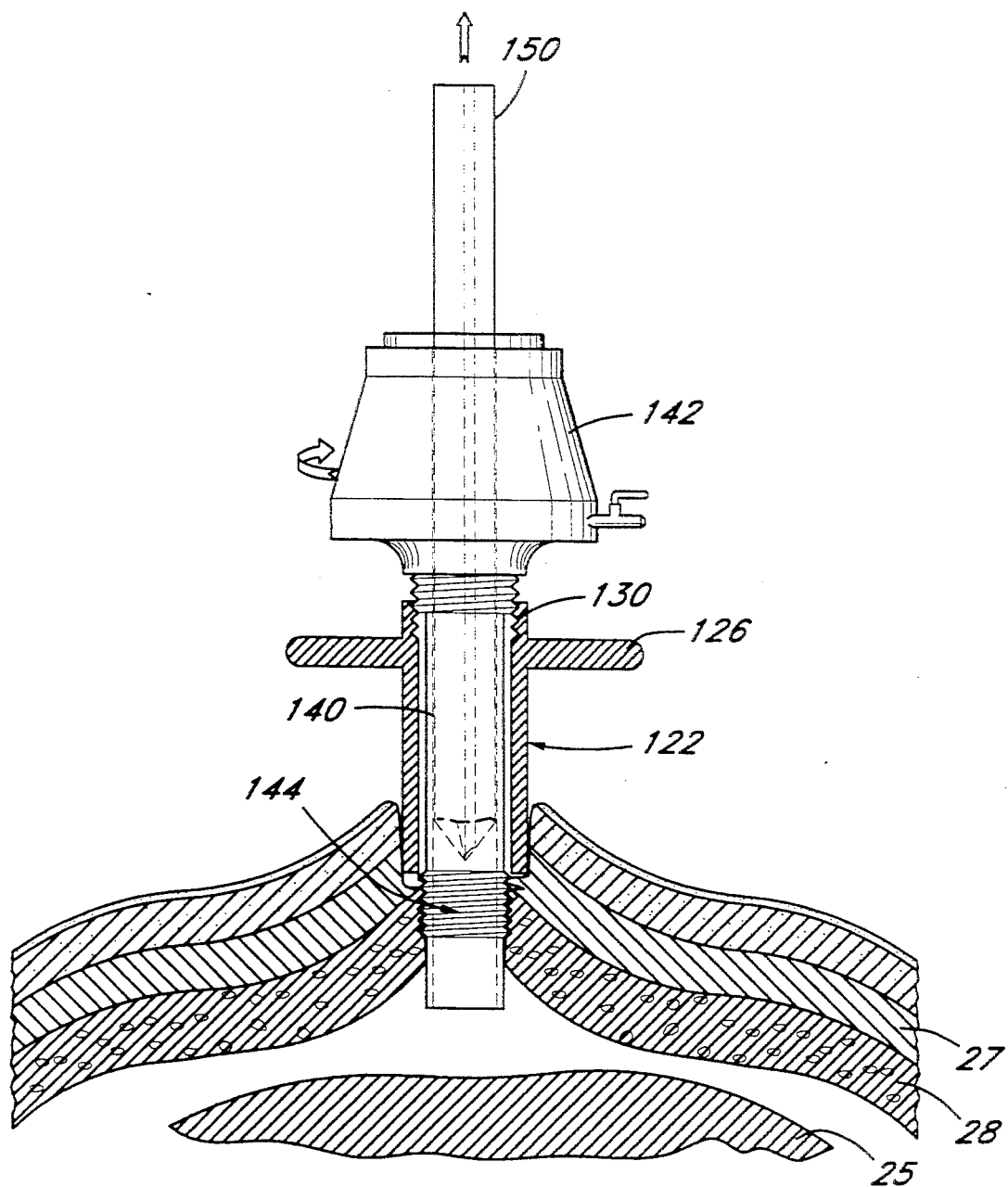

After penetration is achieved, and the trocar 150 is removed, the seal device 144 can be rotated downwardly into place, as shown in FIG. 20, so as to provide an effective seal against the loss of insufflation gas. Rotation of the head piece 142 and cannula 140 will effectively impart rotation to the seal 144 and cause it to advance downward and secure the grip of the walls of the incision 22. Rotation continues until the seal 144 is located at the proper depth, which varies depending on the abundance of fat tissue or lack thereof.

It should be noted that the seal 144 assumes only a frictional fit along the shaft of the cannula 140 so as to be positioned at the appropriate depth for placement in the incision 22. Thus, the length or thickness of the seal 144 can be modified and adjusted on a patient by patient basis depending upon the thickness of the tissue layers of the patient and the degree of seal desired. Therefor, the surgeon may make last minute adjustments to ensure the endoscopic port is complete and ready for use, as illustrated in FIG. 20.

It should also be noted that the head piece 142 of the cannula 140 can be threaded into threads 130 in the proximal portion of the facilitator 122 after location of the seal 144 in order to provide a secure mounting for the head piece 142. Other securing means such as cooperating sliding members adapted to be locked are contemplated. In addition, the secure gripping of the facilitator 122 of this embodiment is such that in many cases it will support itself rigidly or upright in the incision 22, thereby freeing up the hands of the surgeon to perform other procedures. Thus, other endoscopic instruments and the like can be supported in the port without auxiliary ports or manual assistance from the surgeon. In addition, other instruments with adapted screw tips can be threaded into the proximal threaded portion 130 of the facilitator 122.

Figure 21:
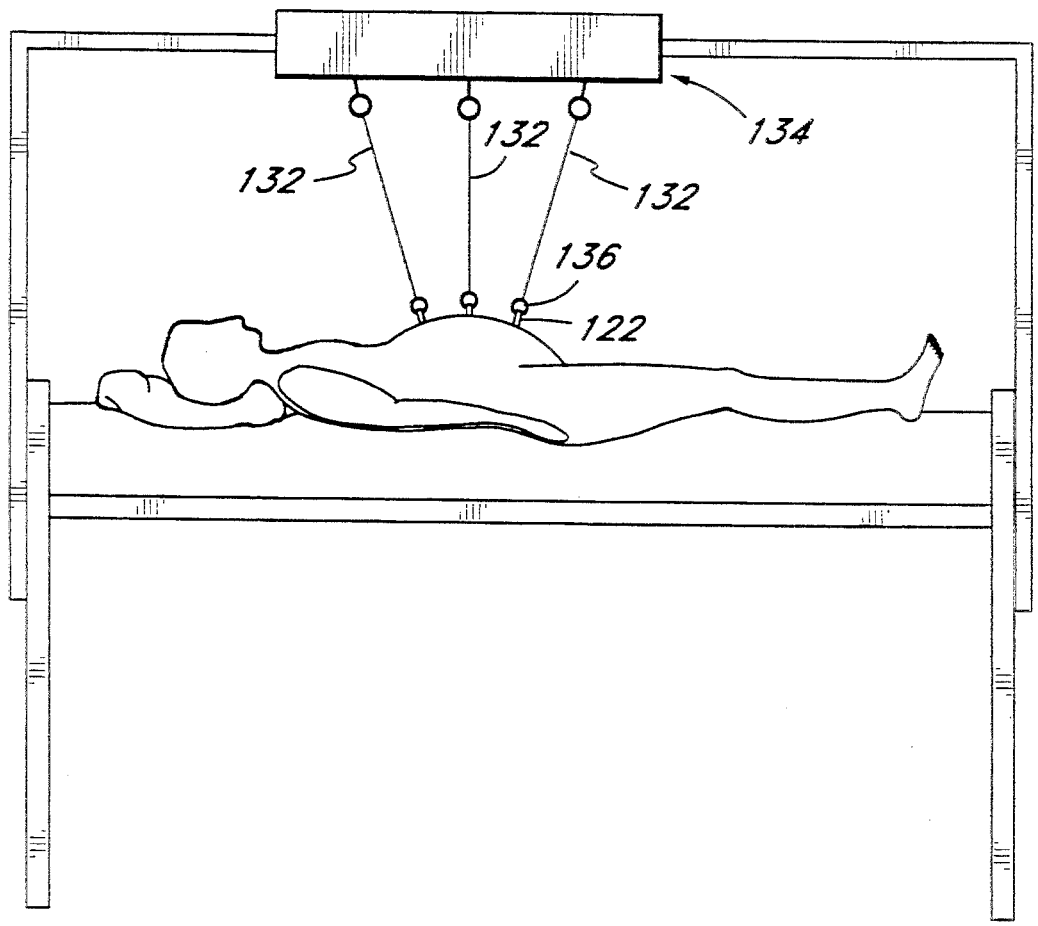

The facilitator 122 of this embodiment, with its oblique gripping action on the fascial tissues 27 of the patient, is sufficiently efficient to eliminate the use of pneumoperitoneum altogether. Thus, as shown in FIG. 21, with the use of several facilitators 122 of this embodiment, the outer tissues of the patient can literally be lifted away from the vital organs 25 and secured by wires 132 to a scaffolding or support mechanism 134, thus avoiding the use of insufflation gas. The placement and number of the facilitators 122, of course, will depend upon the type of endoscopic surgery being conducted. The method for securing the facilitators 122 is the same as explained above in the context of FIGS. 17-20. Also, appropriate rings or loop devices 136 or other tie-down devices can be applied to the facilitators 122 in order to facilitate securing them to the surrounding support structure.

Figure 22:
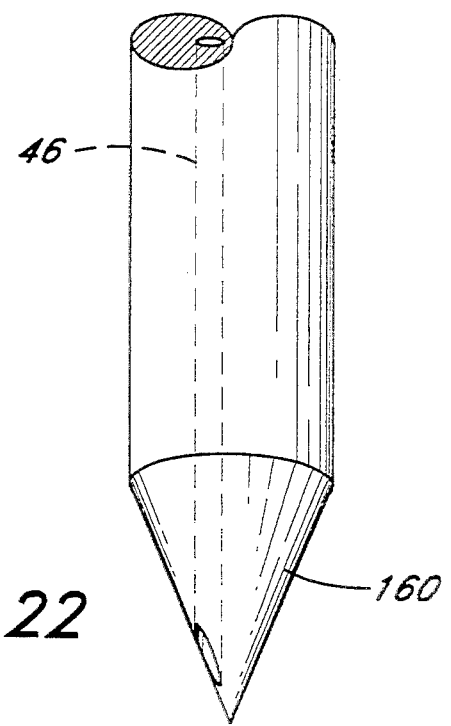
FIG. 22 illustrates an improved trocar tip for use with the trocar facilitator of the present invention.

Trocar of FIG. 22

The present invention also contemplates an improved trocar tip for use in connection with the trocar system of the present invention. Such a trocar tip is illustrated in FIG. 22 and described below in more detail.

It will be noted that in a conventional trocar, the tip is essentially pyramidal, being comprised of three sides or faces, each separated by a sharp edge. Conventional trocar tips are configured in this manner because they cut in three directions along the blade faces, thereby facilitating the ability of the trocar to penetrate the strong, elastic peritoneum. That is, since a substantial amount of force is necessary to pierce the peritoneum, it is understood that this conventional trocar tip will penetrate much more quickly. Surgeons using this tip rely substantially on the momentum that is generated in the hand penetration motion to produce penetration.

However, conventional trocar tips suffer from important disadvantages which are well understandable. First, the blade faces obviously cut the tissues in three directions, generating a larger hole and causing substantial lacerations in the patient's tissues. Although this is a serious disadvantage, it is tolerated because of the need to penetrate the peritoneum as explained above. However, if the opening left by the trocar penetration is not adequately repaired, a herniation at that location may occur or other adhesions may cause substantial pain and discomfort to the patient. An adhesion occurs where the lining of the peritoneum is not smooth, as with scar tissue. Thus, an intestine or other tissue adheres to the peritoneal cavity at the point of trocar penetration and prevents independent movement of the peritoneum separate and apart from that organ.

With the trocar facilitator of the present invention, the need to use an extremely sharp three-sided trocar tip is eliminated. In other words, because of the control provided by the present trocar facilitator, including the use of counter-traction which places the peritoneum in tension to facilitate penetration, a less damaging trocar can be utilized. Thus, as shown in FIG. 22, a conical trocar tip 160 is illustrated which is suitable for use with the trocar facilitator of the present invention.

Since the surgeon need not depend on the momentum of penetration, but can achieve good manual control of the trocar without injury to the internal organs, only a small opening in the peritoneum is created by the trocar tip. Thereafter, possibly with the aid of endoscopic visualization through the trocar port 46 as explained above in more detail, the trocar 160 can be advanced to the degree necessary to generate the endoscopic port. In this manner, the tissues experience less laceration and only a round or circular opening or wound is experienced. This type of wound is much easier to close, thereby reducing the risks associated with adhesions and hernia. In other words, after the initial hole in the peritoneum is formed, the hole is expanded rather than being cut or shredded as with the conventional trocar tip.

Trocar Facilitator of FIGS. 23-31

A trocar facilitator 165 of a fourth embodiment, adapted for use in a trocar system 180, is illustrated in FIGS. 23-31. FIG. 23 illustrates the trocar facilitator 165, which comprises an anchor member 164 having a cylindrical support ring 166 attached to an engaging member or corkscrew-like blade 167, and a lifting member or guide piece 168 comprising two cylindrical guide portions 168a,b having a pair of opposed transverse handles 169 for providing counter-traction. This guide piece 168 has a hollow, cylindrical channel 170 in its center which facilitates the insertion of the trocar, cannula, and other endoscopic surgical devices. At the distal end of the corkscrew-like blade 167, there is shown a sharp point 171. As will be described in more detail below, this sharp point 171 is designed to bore into the layers of tissue in order to provide a secure gripping force for the facilitator 165. As a result, sufficient counter-traction force can be applied to the site of the incision without excessive enlargement of the incision and without the need for deep fascial visualization.

FIG. 24 more clearly illustrates the three pieces which comprise the trocar facilitator 165 of this embodiment. The corkscrew-like blade 167 is attached to a support ring 166, which has internal threads 172 to receive the guide piece 168. This guide piece 168 is comprised of two halves, one half 168a configured with two lateral prongs 173, and the other half 168b configured with openings 174 to receive the two prongs 173. The two pieces 168a,b are assembled by aligning the prongs 173 of one half 168a with the openings 174 in the other 168b, and pushing the two halves toward each other. The assembled guide piece 168 has external threads 175 which fit the support ring of the blade 166 to form a rotary seal which helps to prevent the loss of insufflation gas at the site of penetration.

Figure 25:
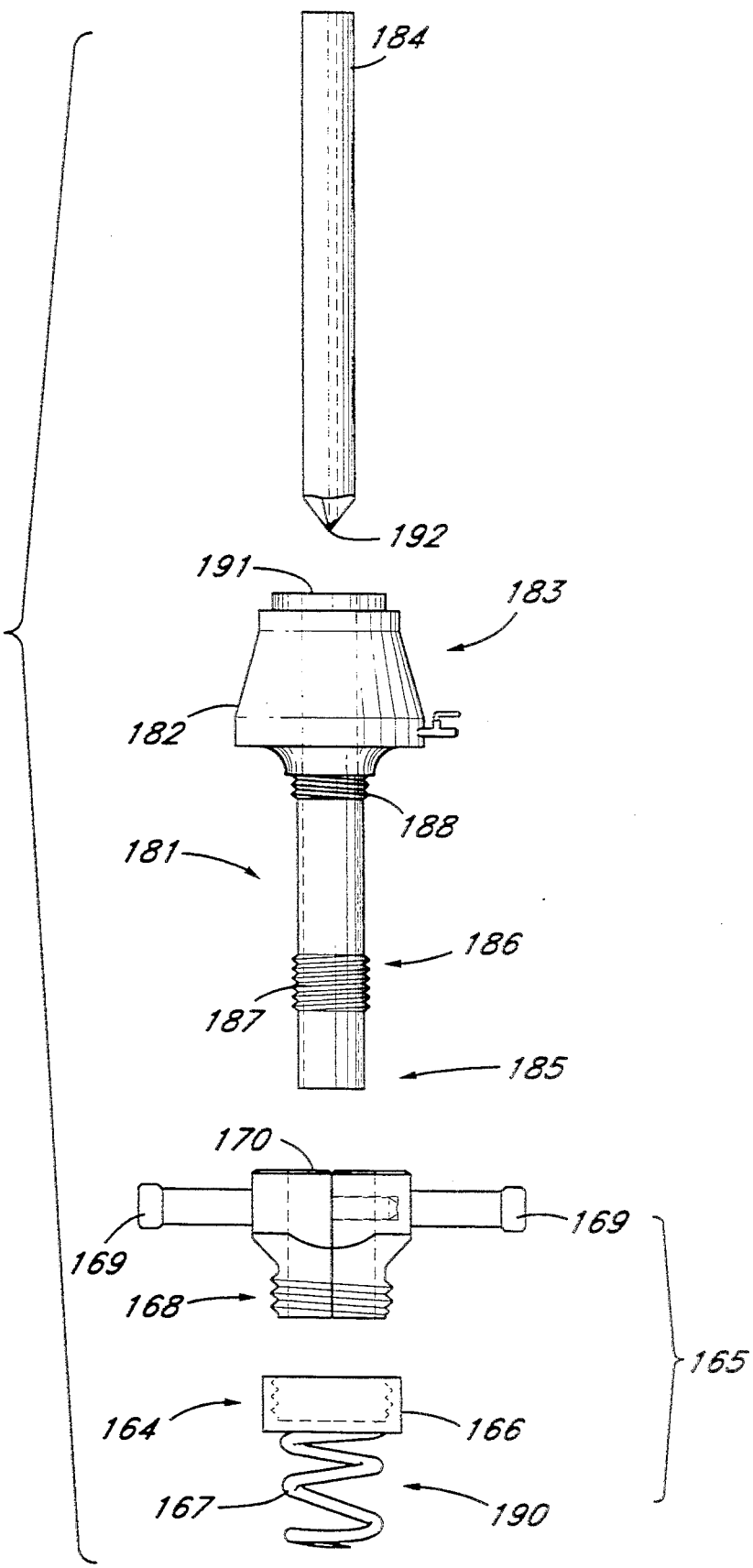
FIG. 25 is a side elevational view of the components of a trocar system, including a trocar, cannula, and trocar facilitator of FIG. 23.

The complete trocar system 180 of this embodiment is illustrated in FIG. 25. The system includes the facilitator 165 described above, the cannula 181 including its associated integral head piece 182 at the proximal end 183, and the trocar 184. Near the distal end 185 of the cannula 181 is a rotary seal 186 having external threads 187 which also help prevent the loss of insufflation gas around the cannula 181 at the site of penetration. The cannula 181 is also provided with external threads 188 at its proximal end near the head piece 182. As explained below in more detail, these external threads 188 engage the internal threads 172 of the anchor member 164 in order to provide a secure anchor-like engagement between the cannula 181 and its head piece 182 and the facilitator 165.

As illustrated in FIG. 25, the trocar facilitator 165 allows for the passage of the cannula 181 through the center of the corkscrew-like blade 190, and through the center of the guide piece 170. The head piece 182 of the cannula 181 contains a flapper valve 191 which allows for the passage of the trocar 184 down through the headpiece 182 and the cannula 181, such that the tip of the trocar 192 is exposed at the distal end of the cannula 185. This valve 191 also acts to prevent the loss of insufflation gas, while allowing for the passage of other endoscopic instruments therethrough. The method of this invention and the manner of use of the trocar system 180 of this embodiment is more fully illustrated in connection with FIGS. 26 and 27.

Figure 26:
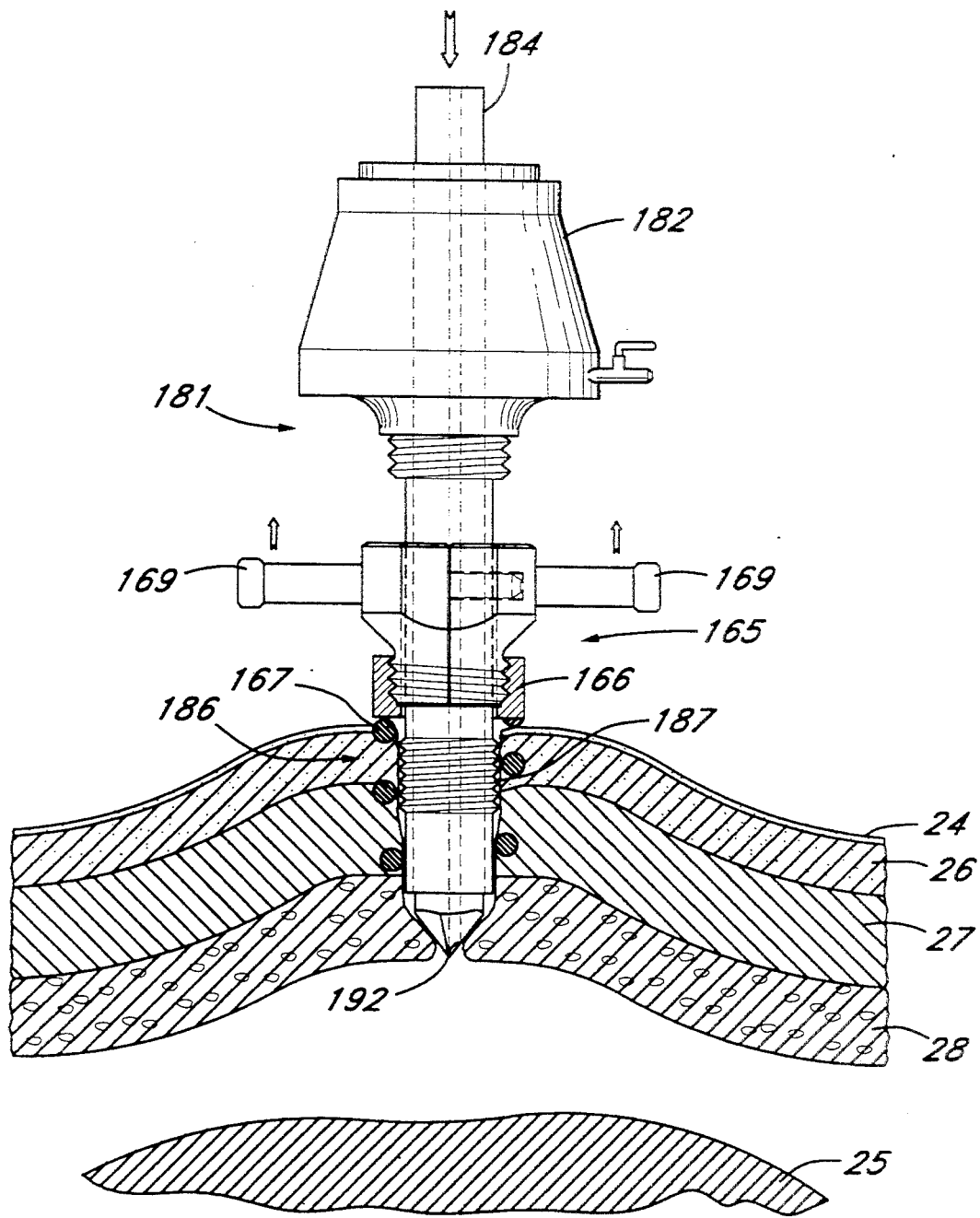
FIGS. 26-27 are partial cross-sectional views illustrating the manner and method of using the trocar facilitator of FIG. 23.

Referring first to FIG. 26, after an initial incision is made, the tip of the assembled trocar facilitator 165 is inserted into the incision to initiate the counter-traction process. The facilitator 165 is rotated by means of its handles 169 in several 360-degree turns. This causes the tissue layers 24, 26, 27, 28 to be threaded onto the corkscrew-like blade 167 of the facilitator 165. In asthenic individuals, the attached support ring 166 will remain on the surface of the body, while in obese individuals it may be necessary that the attached support ring 166 penetrate into the layer of fat 26 so that the sharp tip of the blade 171 is able to penetrate deeply enough to facilitate puncture of the peritoneum 28. Once the facilitator 165 has sufficiently penetrated the tissue layers 24, 26, 27, as shown in FIG. 26, counter-traction can be applied to the handles 169 in order to lift the tissue layers 24, 26, 27, 28 away from the vital organs 25 beneath.

The use of a corkscrew-like blade 167 results in decreased trauma to the fascia 27 and other tissues 24, 26, 28. The lifting force is dispersed vertically along the entire length of the blade 167 and not at the sharp tip only. This helps prevent shredding and laceration of the tissue. The spacing of the turns may be decreased to provide for even more secure lifting, or increased to further reduce trauma to the fascia and other tissues. In addition, silicone or other lubricant may be applied to the length of the blade 167 before insertion into the patient's body to aid in the insertion and reduce the friction on the tissue all along the length of the corkscrew-like blade 167.

As illustrated in FIG. 26, after the blade of the trocar facilitator 167 has been threaded into the layers of tissue 26-27, counter-traction is applied to the handles 169 in order to lift the tissue away from the vital organs 25 beneath. At the same time, the cannula 181 and trocar 184 combination can be passed down through the facilitator 165 and penetration of the trocar 184 through the peritoneum 28 can be accomplished. As explained above in connection with FIG. 19, the rotary seal 186 on the outside of the cannula 181 provides a form of a stop device because of the threads 187 located on the exterior thereof. The threads 187 interfere with the tissues 26, 27 on the side walls of the incision and provide resistance to deeper penetration. This advantage, combined with effective and secure counter-traction, protects the vital organs 25 beneath the tip of the trocar 192.

Figure 27:
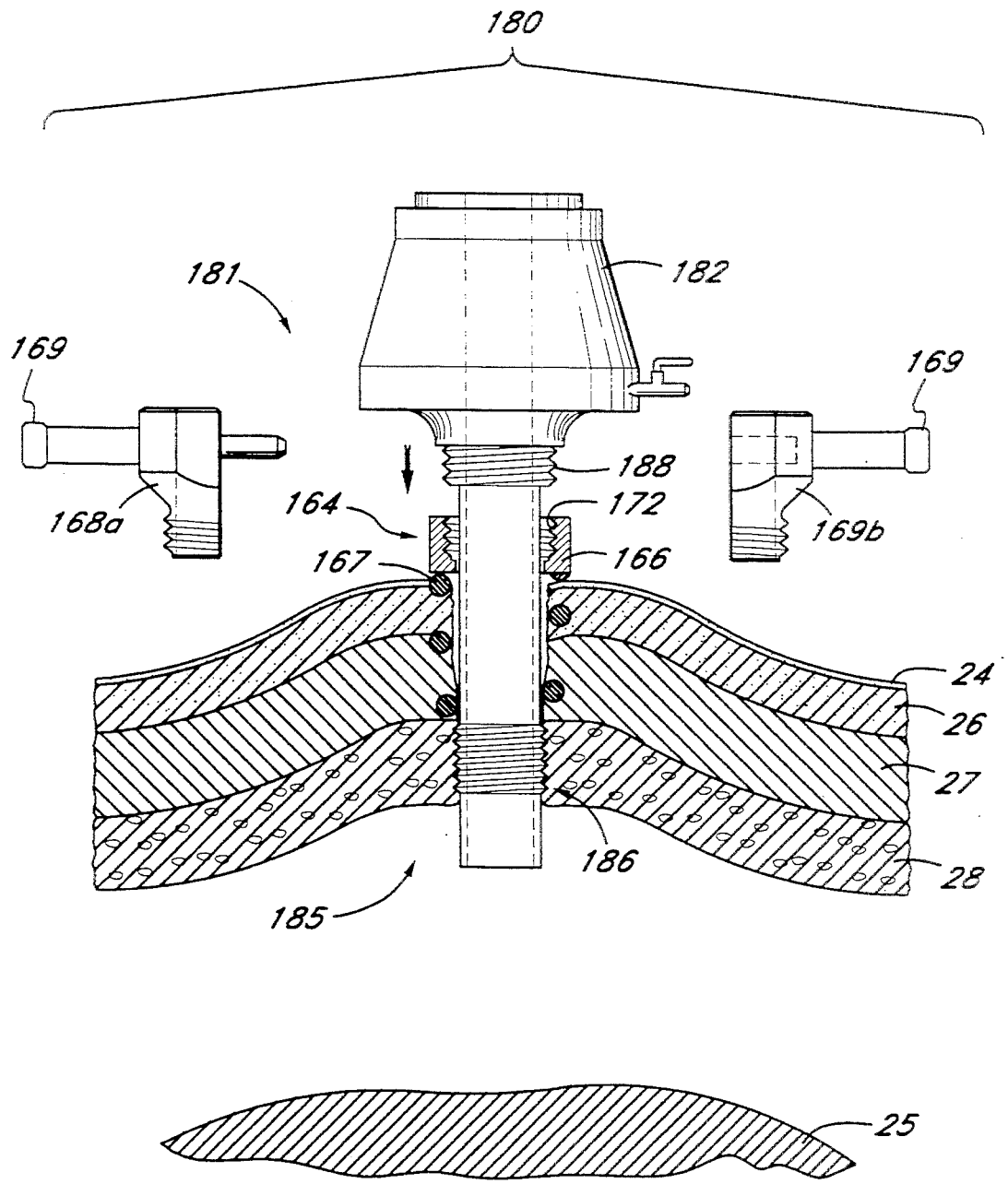

Turning now to FIG. 27, after penetration is achieved and the trocar 184 is removed, the seal device 186 on the distal end of the cannula 185 can be rotated downwardly into place, so as to provide an effective seal against the loss of insufflation gas. Rotation of the head piece 182 and cannula 181 will effectively impart rotation to the seal 186 and cause it to advance downward and secure the grip of the walls of the incision. Rotation continues until the seal 186 is located at the proper depth, which varies depending on the abundance of fat tissue 26 or lack thereof.

After the cannula 181 has been properly positioned, the guide piece 168 of the trocar facilitator 165 may be removed, as illustrated in FIG. 27. This is done by unscrewing the guide piece 168 from the support ring 166, and pulling the two halves 168a,b in opposite directions laterally. The blade of the facilitator 167 remains threaded into the layers of tissue 26, 27. As a result of the secure grip of the corkscrew-like blade 167 of the facilitator 165 and its attached support ring 166, the cannula 181 is supported rigidly in the incision, and the surgeon's hands are kept free. In particular, this secure engagement can be facilitated by the interengagement of the external threads 188 near the proximal end 183 of the cannula 181 and the internal threads 172 of the anchor member 164. In other words, as the cannula 181 and head piece 182 are advanced to the desired depth, in the direction of the arrow shown in FIG. 27, the external threads 188 on the cannula rotatably engage the internal threads 172 to provide a secure anchor for the cannula. Other endoscopic instruments and the like can be supported in the port without the need for auxiliary ports or manual assistance from surgical personnel.

Figure 28:
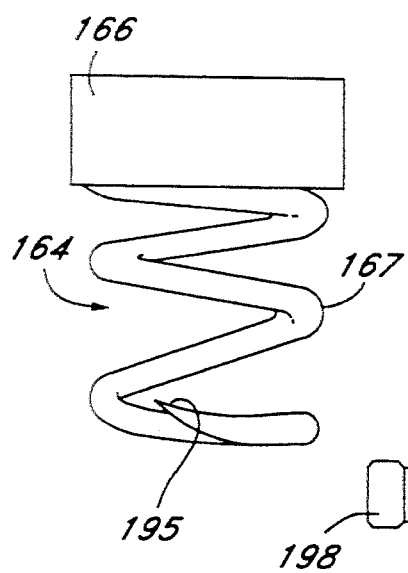
FIG. 28 illustrates an improved tip of the trocar facilitator of the present invention.

In another embodiment of the anchor member 164 of the trocar facilitator 165 of the present invention, illustrated in FIG. 28, the sharp tip 195 of the corkscrew-like blade 167 is angled upward. Entry of the blade 167 into the tissue is advanced by holding the facilitator 165 at an angle, such that the sharp tip 195 is angled downward, into the layers of tissue. Once the facilitator 165 is sufficiently advanced into the tissue, the facilitator 165 is returned to a vertical position, such that the tip of the blade 195 is angled toward the surface of the patient's body. Thus, the vital organs beneath are protected from inadvertent injury by the sharp tip of the blade 195 of the facilitator 165.

Figure 29:
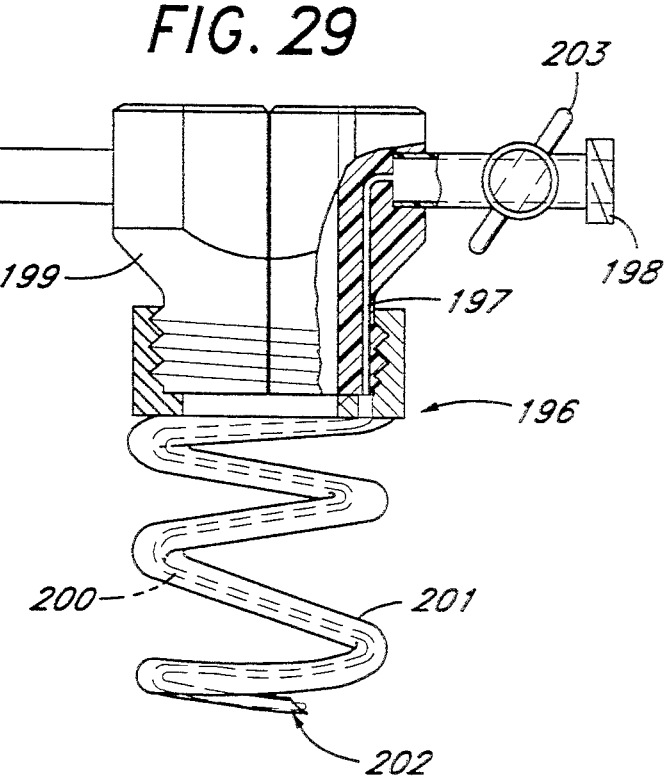
FIG. 29 is a partially cut-away view of the fourth embodiment of the trocar facilitator of the present invention which includes a hollow tube for introducing carbon dioxide gas into the body of the patient.

The present invention also contemplates an improved trocar facilitator 196 designed to eliminate the need for use of a Veress needle to achieve initial insufflation of the abdominal cavity. As illustrated in FIG. 29, the trocar facilitator 196 of the present invention may be configured so as to provide the means for introducing gas into the patient's body. Specifically, the trocar facilitator 196 contains a hollow passageway 197 which travels from the handle of the guide piece 198 through the body of the guide piece 199 and into tubing 200 which runs through the facilitator blade 201 and ends at its tip 202. The hollow handle of the guide piece 198 has an attached stopcock 203 which is used to control the flow of gas.

Figure 30:
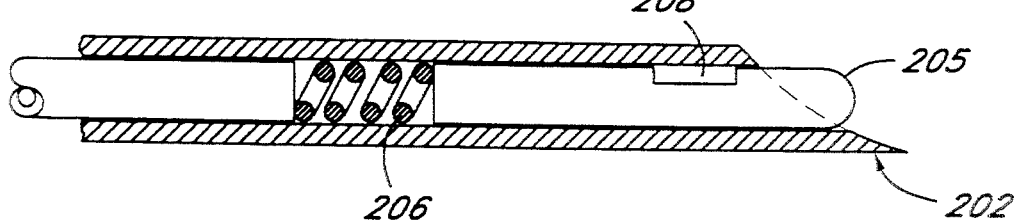
FIG. 30 is an enlarged partial cross-sectional view of the tip of the trocar facilitator of FIG. 29, showing the spring contained in the tip in a compressed position.
Figure 31:
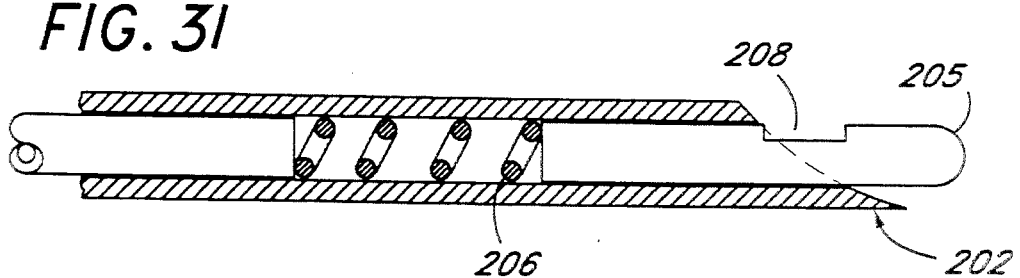
FIG. 31 is an enlarged partial cross-sectional view of the tip of the trocar facilitator of FIG. 29, showing the spring contained in the tip in a relaxed position.

One embodiment of a facilitator blade tip 202 is illustrated in FIGS. 30 and 31. The manner of use of this embodiment of the present invention will now be explained.

As described above in connection with FIGS. 23–27, the trocar facilitator 196 is inserted into the initial incision in the patient's body. The facilitator 196 is rotated, such that the layers of tissue are threaded onto the corkscrew-like blade 201. As the sharp tip of the blade 202 is inserted into the tissue, resistance from the tissue causes the tip of the tubing 205 to be pushed back proximally into the hollow tip of the blade 202, compressing the spring 206 located behind the tip of the tubing 205, as illustrated in FIG. 30. Once the tip of the blade 202 pierces the peritoneum and reaches the space inside the abdominal cavity, however, the resistance from the tissue is eliminated and the spring 206 relaxes, causing the tip of the tubing 205 to extend distally beyond the sharp point of the blade 202. This is illustrated in FIG. 31.

As the tubing 205 extends distally past the tip of the blade 202, as shown in FIG. 31, the opening 208 in the tip of the tubing 205 is exposed. The surgeon then opens the stopcock 203 located on the handle of the trocar facilitator 198, allowing carbon dioxide gas to travel through the facilitator 196 and into the abdominal cavity of the patient. Since the blade of the trocar facilitator 201 remains in place throughout the surgical procedure, insufflation may be increased at any time without the need for introducing any additional instruments or creating any auxiliary ports in the patient's body.

The trocar facilitator 196 of this embodiment thus eliminates the need for a Veress needle and the risks associated with its use. No separate puncture of the patient is necessary, thus reducing trauma to the patient. Risk of inadvertent puncture of vital organs by the needle is eliminated. Because gas may pass through the tubing 200 only when the resistance on the tip of the blade 202 caused by the layers of tissue is eliminated, the risk of pneumo-omentum is reduced. Thus, this embodiment provides several significant advantages over conventional trocar systems.

Although this invention has been described in terms of certain preferred embodiments, it is intended that the scope of the invention not be limited to the specific embodiments set forth herein. Accordingly, the scope of the invention is intended to be defined only by the claims which follow.

What is claimed is:

1. A trocar facilitator for assisting in the establishment of a port for endoscopic surgery through the superficial tissue and peritoneum of a patient's body and for achieving pneumoperitoneum in said body, said port being established by use of a trocar and a cannula, said facilitator comprising:

a guide portion for receiving said trocar and said cannula, said guide portion comprising two releasably engageable halves which form a hollow channel for slidably receiving said trocar and said cannula, said halves being removable from said port without removing said cannula;

a corkscrew-like blade portion removably connected to said guide portion for rotatably engaging said tissue to allow said tissue to be lifted away from vital organs of said patient, and for penetrating said peritoneum of said patient, said blade portion having a proximal and a distal end; and a passageway through said guide and said blade portions, said passageway through said blade portion being helical, whereby gas may be administered through said passageway and into the body of said patient, said passageway having a valve formed near said distal tip, said valve being closed during insertion of said blade portion but open following insertion whereby insufflation gas may pass into the body of the patient.

2. The trocar facilitator of claim 1, wherein said passageway comprises a hollow, flexible tube having a distal and a proximal end.

3. The trocar facilitator of claim 2, wherein said proximal end of said tube remains outside said patient's body, and said distal end of said tube is placed beneath said peritoneum of said patient.

4. The trocar facilitator of claim 2, wherein said distal end of said tube extends distally past the distal end of said blade portion.

5. The trocar facilitator of claim 4, further comprising a spring near said distal end of said tube, such that resistance on said distal end of said tube causes said spring to compress such that said distal end of said tube is displaced proximally behind said distal end of said blade portion.

6. A method of establishing a port for endoscopic surgery through the peritoneum in a patient's body and for achieving pneumoperitoneum in said body, said port being established by use of a trocar and a cannula, comprising:

incising superficial tissue of said body;

inserting a trocar facilitator into said incision, said trocar facilitator comprising:

a guide portion for slidably receiving a trocar and a cannula, said guide portion comprising two releasably engageable halves which form a hollow channel for slidably receiving said trocar and said cannula, whereby following establishment of said port said halves are removable from said port without removing said cannula;

a corkscrew-like blade portion removably connected to said guide portion for rotatably engaging said tissue to allow said tissue to be lifted away from vital organs of said patient, and for and penetrating said peritoneum of said patient, said blade portion having a proximal and a distal end; and a helical passageway through said blade portion, whereby gas may be administered through said passageway and into the body of said patient, said passageway having a valve formed near said distal end, said valve being closed during insertion of said blade but open following insertion whereby insufflation gas may pass into the body of the patient;

rotating said blade portion of said facilitator such that tissue is threaded onto said blade portion and said blade portion remains imbedded in said tissue and said distal end of said blade portion penetrates said peritoneum of said patient;

administering gas through said passageway of said facilitator and beneath said peritoneum.

7. The method of claim 6, further comprising inserting a trocar through said guide and blade portions to further penetrate said superficial tissue and said peritoneum, and inserting a cannula over said trocar to establish said endosurgical port.

8. A trocar facilitator adapted for use with a trocar and a cannula for assisting in the establishment of a port for endoscopic surgery through the superficial tissue and peritoneum of a patient's body and for achieving pneumoperitoneum in said body, comprising:

a guide portion for slidably receiving said trocar and said cannulla, said guide portion comprising a hollow channel for receiving said trocar and said cannula such that said trocar, cannula and guide portion remain slidable relative to each other; and a corkscrew-like blade portion extending distally past said guide portion and removably connected to said guide portion for rotatably engaging said tissue to allow said tissue to be lifted away from vital organs of said patient, and for penetrating said peritoneum of said patient, said blade portion having a helical passageway formed therein;

said blade portion forming a passageway axially aligned with said channel to receive said trocar and said cannula, wherein said helical passageway has a distal end, and further comprises a valve formed near said distal end, said valve being closed during insertion of said blade portion but open following insertion whereby insufflation gas may pass into the body of said patient.

9. A method of establishing a port for endoscopic surgery through the peritoneum in a patient's body and for achieving pneumoperitoneum in said body, said port being established by use of a trocar and a cannula, comprising:

incising superficial tissue of said body;

inserting a trocar facilitator according to claim 8 into said incision;

rotating said trocar facilitator such that tissue is threaded onto said blade portion and said blade portion remains imbedded in said tissue and said distal end of said blade portion penetrates said peritoneum of said patient;

lifting said tissue away from vital organs of said patient by pulling up on said trocar facilitator; and sliding said trocar and then said cannula through said guide portion and through said peritoneum to establish said port.

10. The method of claim 9, further comprising allowing gas to pass through said helical passageway formed within said corkscrew-like blade portion, and below said peritoneum to produce pneumoperitoneum in said patient.

* * * * *